(12) United States Patent
Wang et al.

(10) Patent No.: US 9,745,314 B2
(45) Date of Patent: Aug. 29, 2017

(54) MDM2 INHIBITORS AND THERAPEUTIC METHODS USING THE SAME

(71) Applicant: THE REGENTS OF THE UNIVERSITY OF MICHIGAN, Ann Arbor, MI (US)

(72) Inventors: Shaomeng Wang, Saline, MI (US); Angelo Aguilar, Ann Arbor, MI (US); Liu Liu, Ann Arbor, MI (US); Jianfeng Lu, Ann Arbor, MI (US); Donna McEachern, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/688,553

(22) Filed: Apr. 16, 2015

(65) Prior Publication Data

US 2015/0299211 A1  Oct. 22, 2015

Related U.S. Application Data

(60) Provisional application No. 61/980,747, filed on Apr. 17, 2014.

(51) Int. Cl.
| | |
|---|---|
| C07D 487/10 | (2006.01) |
| C07D 209/96 | (2006.01) |
| C07D 209/54 | (2006.01) |
| A61K 31/404 | (2006.01) |
| A61K 31/407 | (2006.01) |
| A61K 45/06 | (2006.01) |
| A61N 5/10 | (2006.01) |

(52) U.S. Cl.
CPC .......... *C07D 487/10* (2013.01); *A61K 31/407* (2013.01); *A61K 45/06* (2013.01); *A61N 5/10* (2013.01); *A61N 2005/1098* (2013.01)

(58) Field of Classification Search
CPC .. C07D 487/10; C07D 209/96; C07D 209/54; A61K 31/4035; A61K 31/407; A61K 31/404
USPC ........ 548/408, 410, 453, 467, 486; 206/223, 206/232; 514/409, 413, 418, 414, 421
See application file for complete search history.

(56) References Cited

U.S. PATENT DOCUMENTS

| | | | |
|---|---|---|---|
| 3,989,816 A | 11/1976 | Rajadhyaksha | |
| 4,444,762 A | 4/1984 | Rajadhyaksha | |
| 5,770,581 A | 6/1998 | Weichselbaum et al. | |
| 7,737,174 B2 | 6/2010 | Wang et al. | |
| 7,759,383 B2 | 7/2010 | Wang et al. | |
| 7,851,626 B2 | 12/2010 | Ding et al. | |
| 8,088,815 B2 | 1/2012 | Bartkovitz et al. | |
| 8,088,931 B2 | 1/2012 | Wang et al. | |
| 8,222,288 B2 | 7/2012 | Wang et al. | |
| 8,629,141 B2* | 1/2014 | Wang ................... | C07D 487/10 514/232.8 |
| 8,680,132 B2 | 3/2014 | Wang et al. | |
| 8,742,121 B2 | 6/2014 | Wang et al. | |
| 8,877,796 B2 | 11/2014 | Wang et al. | |
| 8,901,117 B2 | 12/2014 | Wang et al. | |
| 2006/0211757 A1 | 9/2006 | Wang et al. | |
| 2008/0206794 A1 | 8/2008 | Hu et al. | |
| 2010/0075948 A1 | 3/2010 | Ding et al. | |
| 2010/0152190 A1 | 6/2010 | Bartkovitz et al. | |
| 2010/0273799 A1 | 10/2010 | Wang et al. | |
| 2011/0112052 A1 | 5/2011 | Wang et al. | |
| 2011/0130398 A1 | 6/2011 | Bartkovitz et al. | |
| 2012/0046306 A1 | 2/2012 | Bartkovitz et al. | |
| 2012/0101092 A1 | 4/2012 | Wang et al. | |
| 2012/0122947 A1 | 5/2012 | Wang et al. | |
| 2012/0289494 A1* | 11/2012 | Wang ................... | C07D 487/10 514/210.18 |
| 2013/0030173 A1 | 1/2013 | Wang et al. | |
| 2013/0296303 A1 | 11/2013 | Wang et al. | |
| 2014/0148494 A1 | 5/2014 | Wang et al. | |
| 2014/0378680 A1 | 12/2014 | Wang et al. | |

FOREIGN PATENT DOCUMENTS

| | | |
|---|---|---|
| WO | WO-2011/153509 A1 | 12/2011 |
| WO | WO-2013/049250 A1 | 4/2013 |

OTHER PUBLICATIONS

Stepan et al. "Application of the bicyclo[1.1.1]pentane motif as a nonclassical phenyl ring bioisostere in the design of a potent and orally active y-secretase inhibitor", J. Med. Chem. (2012), 55(7), pp. 3414-3424.*
Berge et al., Pharmaceutical salts, J. Pharm. Sci., 66(1):1-19 (1977).
Dimri, What has senescence got to do with cancer?, Cancer Cell, 7(6):505-12 (2005).
Ding et al., Discovery of RG7388, a potent and selective p53-MDM2 inhibitor in clinical development, J. Med. Chem., 56(14):5979-83 (2013).
Garcia-Echeverria et al., Discovery of potent antagonists of the interaction between human double minute 2 and tumor suppressor p53, J. Med. Chem., 43(17):3205-8 (2000).
Gonzalez-Lopez de Turiso et al., Rational design and binding mode duality of MDM2-p53 inhibitors, J. Med. Chem., 56(10):4053-70 (2013).
Lowe et al., Apoptosis in cancer, Carcinogenesis, 21(3):485-95 (2000).
Ma et al., Asymmetric dipolar cycloaddition reactions: a practical, convergent synthesis of chiral pyrrolidines, Tetrahedron: Asymmetry, 8(6):883-7 (1997).

(Continued)

*Primary Examiner* — Alicia L Otton
*Assistant Examiner* — Sagar Patel
(74) *Attorney, Agent, or Firm* — Marshall, Gerstein & Borun LLP

(57) ABSTRACT

Inhibitors of MDM2 and MDM2-related proteins and compositions containing the same are disclosed. Methods of using the MDM2 inhibitors in the treatment of diseases and conditions wherein inhibition of an interaction between p53 and MDM2 provides a benefit, like cancers, also are disclosed.

26 Claims, 2 Drawing Sheets

(56) References Cited

OTHER PUBLICATIONS

Nicholson, From bench to clinic with apoptosis-based therapeutic agents, Nature, 407(6805):810-6 (2000).
Ponder, Cancer genetics, Nature, 411(6835):336-41 (2001).
Rew et al., Structure-based design of novel inhibitors of the MDM2-p53 interaction, J. Med. Chem., 55(11):4936-54 (2012).
Shu et al., Synthesis of a spiroindolinone pyrrolidinecarboxamide MDM2 antagonist, Org. Process Res. Dev., 17(2):247-56 (2013).
Stepan et al., Application of the bicyclo[1.1.1]pentane motif as a nonclassical phenyl ring bioisostere in the design of a potent and orally active γ-secretase inhibitor, J. Med. Chem., 55(7):3414-24 (2012).
Sun et al., Discovery of AMG 232, a potent, selective, and orally bioavailable MDM2-p53 inhibitor in clinical development, J. Med. Chem., 57(4):1454-72 (2014).
Vassilev et al., In vivo activation of the p53 pathway by small-molecule antagonists of MDM2, Science, 303(5659):844-8 (2004).
Vogelstein et al., Surfing the p53 network, Nature, 408(6810):307-10 (2000).
Vu et al., Discovery of RG7112: A Small-Molecule MDM2 Inhibitor in Clinical Development, ACS Med. Chem. Lett., 4(5):466-9 (2013).
Wu et al., The p53-mdm-2 autoregulatory feedback loop, Genes Dev., 7(7A):1126-32 (1993).
Zhang et al., Discovery of Potent and Orally Active p53-MDM2 Inhibitors RO5353 and RO2468 for Potential Clinical Development, ACS Med. Chem. Lett., 5(2):124-7 (2013).
Zhao et al., A potent small-molecule inhibitor of the MDM2-p53 interaction (MI-888) achieved complete and durable tumor regression in mice, J. Med. Chem., 56(13):5553-61 (2013).
Zhao et al., Diastereomeric spirooxindoles as highly potent and efficacious MDM2 inhibitors, J. Am. Chem. Soc., 135(19):7223-34 (2013).

\* cited by examiner

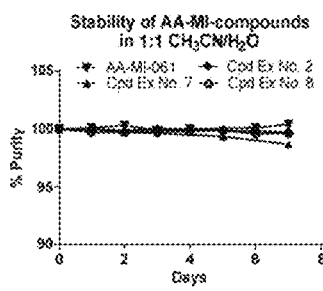
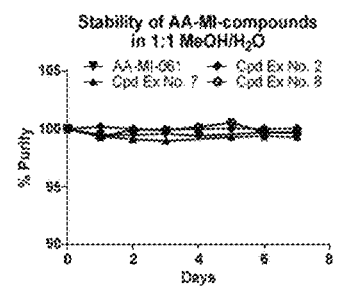
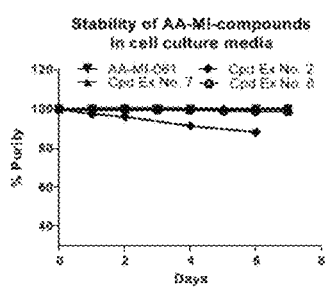

Chemical stability comparison of AA-MI-061, Cpd Ex No. 2, Cpd Ex No. 7 and Cpd Ex No. 8 in Figure 1A. 1:1 $CH_3CN$ to $H_2O$; Figure 1B. 1:1 MeOH to $H_2O$; and Figure 1C. cell culture media

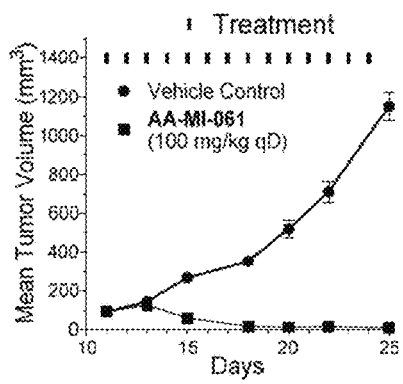
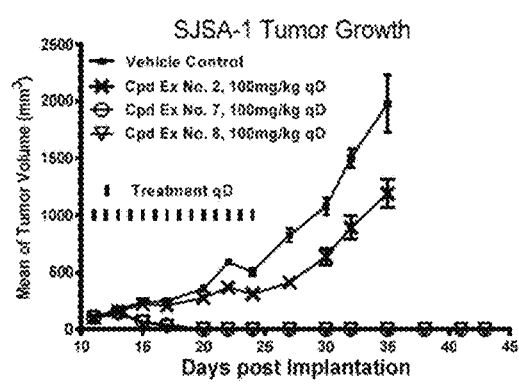

Efficacy in the SJSA-1 xenograft model in mice of Figure 2A. AA-MI-061 achieving 90% tumor regression; and Figure 2B. Compound No. 2 showing partial tumor growth inhibition, and Compounds No. 7 and No. 8 demonstrating complete (100%) tumor regression.

Efficacy in the SJSA-1 xenograft model in mice of Compound No. 8. Compound No. 8 demonstrated tumor regression with different dosing schedules (e.g., daily at 100 mg/kg, every other day at 200 mg/kg, and days 1-3 per week).

MDM2 INHIBITORS AND THERAPEUTIC METHODS USING THE SAME

CROSS-REFERENCE TO RELATED APPLICATIONS

This application claims the benefit of U.S. Provisional Patent Application No. 61/980,747, filed Apr. 17, 2014, which is incorporated by reference herein in its entirety.

FIELD OF THE INVENTION

The present invention relates to inhibitors of MDM2 and MDM2-related proteins and to therapeutic methods of treating conditions and diseases wherein inhibition of MDM2 and MDM2-related proteins provides a benefit.

BACKGROUND OF THE INVENTION

The aggressive cancer cell phenotype is the result of a variety of genetic and epigenetic alterations leading to deregulation of intracellular signaling pathways (Ponder, *Nature* 411:336 (2001)). Cancer cells typically fail to execute an apoptotic program, and lack of appropriate apoptosis due to defects in the normal apoptosis machinery is considered a hallmark of cancer (Lowe et al., *Carcinogenesis* 21:485 (2000)). The inability of cancer cells to execute an apoptotic program due to defects in the normal apoptotic machinery often is associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., *Carcinogenesis* 21:485 (2000); Nicholson, *Nature* 407:810 (2000)). Accordingly, current and future efforts directed to designing and developing new molecular target-specific anticancer therapies to improve survival and quality of life of cancer patients must include strategies that specifically target cancer cell resistance to apoptosis.

The p53 tumor suppressor plays a central role in controlling cell cycle progression, senescence, and apoptosis (Vogelstein et al., *Nature* 408:307 (2000); Goberdhan, *Cancer Cell* 7:505 (2005)). MDM2 and p53 are part of an autoregulatory feed-back loop (Wu et al., *Genes Dev.* 7:1126 (1993)). MDM2 is transcriptionally activated by p53 and MDM2, in turn, inhibits p53 activity by at least three mechanisms (Wu et al., *Genes Dev.* 7:1126 (1993)). First, MDM2 protein directly binds to the p53 transactivation domain, and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation.

Although high-affinity peptide-based inhibitors of MDM2 have been successfully designed in the past (Garcia-Echeverria et al., *Med. Chem.* 43:3205 (2000)), these inhibitors are not suitable therapeutic molecules because of their poor cell permeability and in vivo bioavailability. In the last few years, there have been reports of discoveries of potent, non-peptide, small-molecule MDM2 inhibitors. See e.g., U.S. Pat. Nos. 7,851,626; 8,088,815; 7,759,383; 7,737,174; and 8,629,141; U.S. Pat. Appl. Publ. Nos. 2012/0046306; 2010/0152190; 2011/0112052; 2012/0122947; Int. Pat. Appl. Publ. WO 2011/153509; WO 2013/049250; literature, Vassilev et al. Science 2004, 303, 844-48; Vu, et al. ACS Med. Chem. Lett., 2013, 4 (5), 466-69; Zhang, et al. ACS Med. Chem. Lett., 2014, 5 (2), 124-27; Ding et. al., J. Med. Chem., 2013, 56 (14), 5979-83; Shu, et al. Org. Process Res. Dev., 2013, 17 (2), 247-56; Zhao, et al. J. Med. Chem., 2013, 56 (13), 5553-61; Zhao, et al. J. Am. Chem. Soc., 2013, 135 (19), 7223-34; Sun et al. J. Med. Chem., 2014, 57 (4), 1454-72; Turiso et al., J. Med. Chem., 2013, 56 (10), 4053-70; and Rew et al. J. Med. Chem., 2012, 55 (11), 4936-54). Despite these major advances, there is still a need to identify potent, non-peptide MDM2 inhibitors having suitable physiochemical and pharmacological properties that permit use of the inhibitors in therapeutic applications.

The present invention provides compounds designed to inhibit MDM2-p53 interactions, and therefore activate the function of p53 and p53-related proteins for therapeutic applications.

SUMMARY OF THE INVENTION

The present invention is directed to inhibitors of MDM2 and MDM2-related proteins, to compositions comprising the inhibitors, and to methods of using the inhibitors in a therapeutic treatment of conditions and diseases wherein inhibition of MDM2 and MDM2-related proteins activity provides a benefit.

The present invention therefore provides compounds of structural formula (I) that not only demonstrate improvement in their chemical solution stability but also exhibited an unexpected improved anti-tumor activity, including achieving complete tumor regression in an animal model of human osteosarcoma.

More particularly, the present invention is directed to compounds having a structural formula (I):

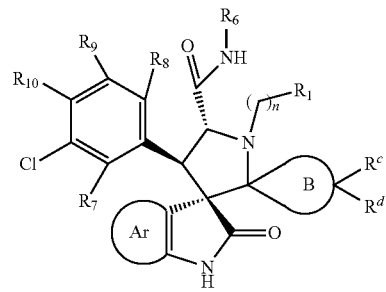

wherein

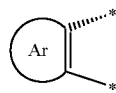

is selected from the group consisting of

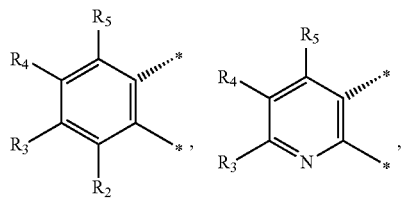

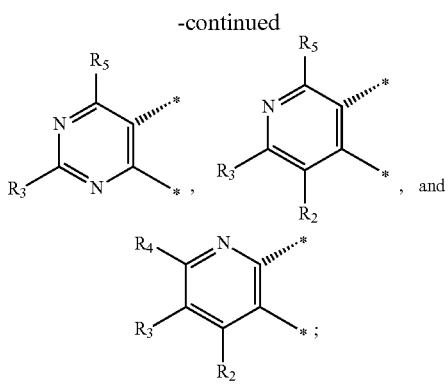

B is a C$_{4-7}$ carbocyclic ring;

R$_1$ is H, substituted or unsubstituted C$_{1-4}$alkyl, substituted or unsubstituted cycloalkyl, substituted or unsubstituted heterocycloalkyl, OR$^a$, or NR$^a$R$^b$;

n is 0, 1, or 2;

R$_2$, R$_3$, R$_4$, R$_5$, R$_7$, R$_8$, R$_9$, and R$_{10}$, independently, are selected from the group consisting of H, F, Cl, CH$_3$, and CF$_3$;

R$_6$ is

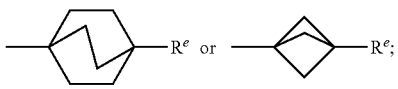

R$^a$ is hydrogen or substituted or unsubstituted C$_{1-4}$alkyl;

R$^b$ is hydrogen or substituted or unsubstituted C$_{1-4}$alkyl;

R$^c$ and R$^d$ are substituents on one carbon atom of ring B, wherein

R$^c$ is H, C$_{1-3}$alkyl, C$_{1-3}$alkyleneOR$^a$, OR$^a$, or halo;

R$^d$ is H, C$_{1-3}$alkyl, C$_{1-3}$alkyleneOR$^a$, OR$^a$, or halo; or

R$^c$ and R$^d$ are taken together with the carbon to which they are attached to form a 4 to 6-membered Spiro substituent, optionally containing an oxygen atom; and R$^e$ is —C(=O)OR$^a$, —C(=O)NR$^a$R$^b$, or —C(=O)NHSO$_2$CH$_3$, or a pharmaceutically acceptable salt thereof.

In one embodiment, the present invention provides a method of treating a condition or disease by administering a therapeutically effective amount of a compound of structural formula (I) to an individual in need thereof. The disease or condition of interest is treatable by inhibition of MDM2 and MDM-2 related proteins, for example, a cancer or a hyperproliferative disorder.

The compounds of structural formula (I) inhibit the interaction between p53 or p53-related proteins and MDM2 or MDM2-related proteins. Therefore, in another embodiment, methods are provided to induce senescence, cell cycle arrest, and/or apoptosis in cells containing functional p53 or p53-related proteins comprising contacting the cells with a compound of structural formula (I).

Still another embodiment is to provide methods of treating, ameliorating, or preventing a hyperproliferative disease, e.g., a cancer, for example, adrenal cortical cancer, advanced cancer, anal cancer, aplastic anemia, bile duct cancer, bladder cancer, bone cancer, bone metastasis, brain/CNS tumors in adults, brain/CNS tumors in children, breast cancer, breast cancer in men, cancer in children, cancer of unknown primary, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal and hypopharyngeal cancer, leukemia—acute lymphocytic (ALL) in adults, leukemia—acute myeloid (AML), leukemia—chronic lymphocytic (CLL), leukemia—chronic myeloid (CML), leukemia—chronic myelomonocytic (CMML), leukemia in children, liver cancer, lung cancer—non-small cell, lung cancer—small cell, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, non-Hodgkin lymphoma in children, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer—basal and squamous cell, skin cancer—melanoma, small intestine cancer, stomach cancer, testicular cancer, thymus cancer, thyroid cancer, uterine sarcoma, vaginal cancer, vulvar cancer, Waldenstrom macroglobulinemia, or Wilms Tumor, in a patient comprising administering to the patient a compound of structural formula (I).

Another embodiment of the present invention is to provide a composition comprising (a) an MDM2 inhibitor of structural formula (I) and (b) an excipient and/or pharmaceutically acceptable carrier.

Another embodiment of the present invention is to utilize a composition comprising a compound of structural formula (I) and a second therapeutically active agent in a method of treating an individual for a disease or condition wherein inhibition of MDM2 and MDM2-related proteins provides a benefit.

In another embodiment, methods of protecting normal (e.g., non-hyperproliferative) cells in a mammal from the toxic side effects of chemotherapeutic agents and treatments are provided. This method comprises administering to the mammal or therapeutically-effective amount of one or more compound of structural formula (I).

In a further embodiment, the invention provides for use of a composition comprising an MDM2 inhibitor of structural formula (I) and an optional second therapeutic agent for the manufacture of a medicament for treating a disease or condition of interest, e.g., a cancer.

Still another embodiment of the present invention is to provide a kit for human pharmaceutical use comprising (a) a container, (b1) a packaged composition comprising an MDM2 inhibitor of structural formula (I), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

An MDM2 inhibitor of structural formula (I) and the second therapeutic agent, e.g., an anticancer agent, can be administered together as a single-unit dose or separately as multi-unit doses, wherein the MDM2 inhibitor of structural formula (I) is administered before the second therapeutic agent or vice versa. It is envisioned that one or more dose of an MDM2 inhibitor of structural formula (I) and/or one or more dose of a second therapeutic agent can be administered.

In one embodiment, an MDM2 inhibitor of structural formula (I) and a second therapeutic agent are administered simultaneously. In related embodiments, an MDM2 inhibitor of structural formula (I) and a second therapeutic agent are administered from a single composition or from separate compositions. In a further embodiment, the MDM2 inhibitor of structural formula (I) and second therapeutic agent are administered sequentially. An MDM2 inhibitor of structural formula (I), as used in the present invention, can be administered in an amount of about 0.005 to about 500 milligrams per dose, about 0.05 to about 250 milligrams per dose, or about 0.5 to about 100 milligrams per dose.

These and other embodiments and features of the present invention will become apparent from the following detailed description of the preferred embodiments.

BRIEF DESCRIPTION OF DRAWINGS

FIG. 1A contains a graph of % purity vs. time (days) for compounds AA-MI-061, Cpd No. 2, Cpd No. 7, and Cpd No. 8 in 1:1 $CH_3CN/H_2O$.

FIG. 1B contains a graph of % purity vs. time (days) for compounds AA-MI-061, Cpd No. 2, Cpd No. 7, and Cpd No. 8 in 1:1 $MeOH/H_2O$.

FIG. 1C contain graphs of % purity vs. time (days) for compounds AA-MI-061, Cpd No. 2, Cpd No. 7, and Cpd No. 8 in cell culture media.

FIG. 2A contains a graph of mean tumor volume ($mm^3$) vs. time (days) showing the efficacy of various tested compounds for tumor regression in the SJSA-1 xenograft model.

FIG. 2B contains a graph of mean tumor volume ($mm^3$) vs. time (days) showing the efficacy of various tested compounds for tumor regression in the SJSA-1 xenograft model.

DETAILED DESCRIPTION OF THE PREFERRED EMBODIMENTS

Figure 3:
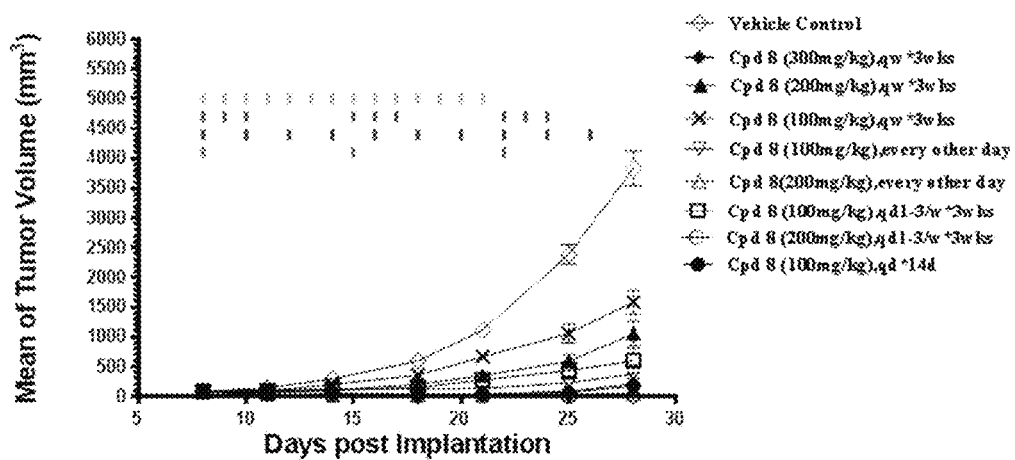
FIG. 3 contains a graph of mean tumor volume ($mm^3$) vs. time (days) showing the efficacy of various doses and dose schedules of Cpd No. 8 for tumor regression in the SJSA-1 xenograft model.

Spiro-oxindole-based antagonists are a class of inhibitors of the p53-MDM2 interaction and are described in U.S. Pat. Nos. 7,759,383, 7,737,174, and 8,629,141. Some spiro-oxindole MDM2 inhibitors quickly converted, in protic solution, from one diastereomer to three other diastereomers (Zhao, et al. J Am Chem Soc. 2013, 135(19):7223-34). Efforts were made to improve the chemical stability of spiro-oxindole MDM2 inhibitors, such as those described in U.S. Pat. No. 8,629,141. For example, compounds shown in Scheme 1 were shown to quickly isomerize from less potent diastereomers to more potent and chemically more stable diastereomers as MDM2 inhibitors in U.S. Pat. No. 8,629,141.

Scheme 1. Conversion of less potent diastereomers to MDM2 to more potent diastereomers to MDM2

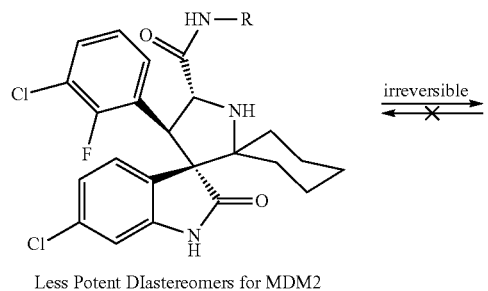

Less Potent DIastereomers for MDM2

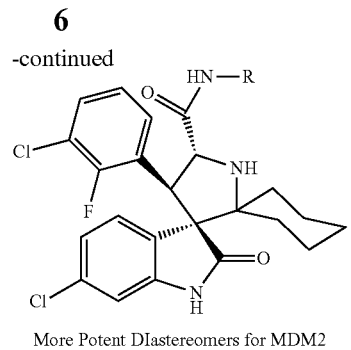

More Potent DIastereomers for MDM2

When the carboxamide substituent R is a benzoic acid, such as in AA-MI-061, the compound demonstrated high binding affinity to MDM2, potent cell growth inhibition in SJSA-1 cells and 90% tumor regression (at 100 mg/kg, once, daily dosing) in SCID mice bearing SJSA-1 xenografts (FIG. 2A). Several other classes of spiro-oxindole compounds (U.S. Pat. Appl. Publ. 2011, US 20110130398, Shu et al. Org. Process Res. Dev., 2013, 17 (2), 247-56, and Zhang et al. ACS Med. Chem. Lett., 2014, 5 (2), 124-27) and pyrrolidines (Ding et. al J. Med. Chem., 2013, 56 (14), 5979-83, and U.S. Pat. Appl. Publ. US 20100152190, 2010) that contain the benzoic acid carboxamide substituent have shown high binding affinities to MDM2, good oral pharmacokinetics in animals, and strong antitumor activity in animal models of human cancer. These prompted us to explore replacements for the benzoic acid group for the design of new MDM2 inhibitors (Scheme II).

Scheme 2. New MDM2 inhibitors designed using replacements of the benzoic acid group.

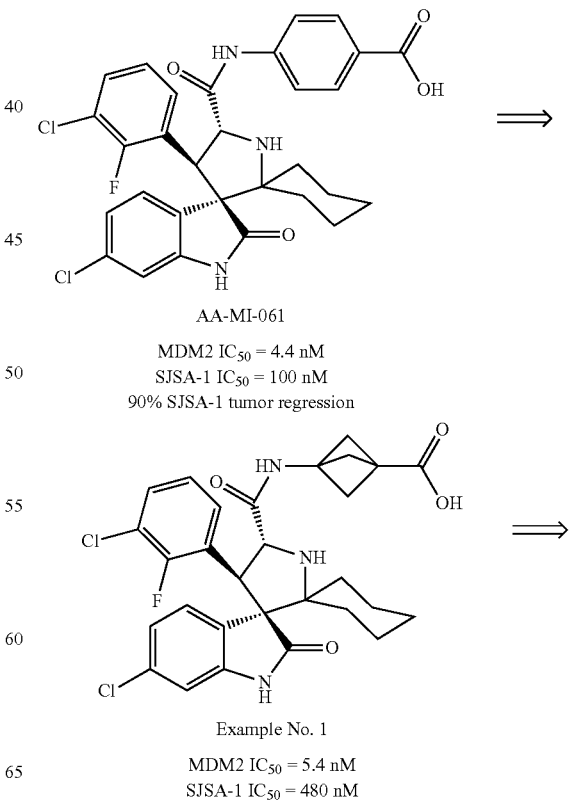

AA-MI-061

MDM2 $IC_{50}$ = 4.4 nM
SJSA-1 $IC_{50}$ = 100 nM
90% SJSA-1 tumor regression

Example No. 1

MDM2 $IC_{50}$ = 5.4 nM
SJSA-1 $IC_{50}$ = 480 nM

-continued

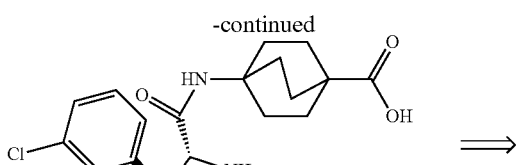

Example No. 2

MDM2 IC$_{50}$ = 5.2 nM
SJSA-1 IC$_{50}$ = 89 nM
tumor growth inhibition

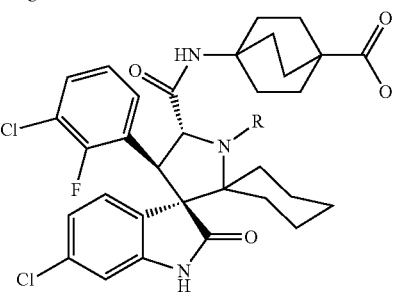

R = Me, Example No. 7
R = Et, Example No. 8

MDM2 IC$_{50}$ = <5 nM
SJSA-1 IC$_{50}$ = <70 nM
complete and presisnt
tumor regression In accordance with the present invention, the benzoic acid substituent of the carboxamide in AA-MI-061 was replaced with non-classical benzoic acid bioisosteres (J. Med. Chem. 2012, 55, 3414), such as a bicyclo[1.1.1]pentane-1-carboxylic acid group or a bicyclo[2.2.2]octane-1-carboxylic acid group, that produced Compound No. 1 and Compound No. 2, respectively (Scheme 2). While, Compound No. 1 maintained a high binding affinity to MDM2 protein, it had a reduced potency in the cell growth inhibition activity in SJSA-1 cells, compared to AA-MI-061. On the other hand, Compound No. 2, containing a bicyclo[2.2.2]octane-1-carboxylic acid group, maintained high binding affinity to MDM2 protein, and potent cell growth inhibition activity in SJSA-1 cells, similar to the potency obtained for AA-MI-061. Compound No. 2, however, still showed only modest anti-tumor activity, merely inhibiting growth in mice bearing the SJSA-1 xenograft tumors without achieving tumor regression (FIG. 2B).

In an effort to improve the antitumor activity of Compound No. 2 in animals, alkylation of the pyrrolidine nitrogen produced a series of compounds, including Compounds No. 7 and No. 8. Compounds No. 7 and No. 8 retained high binding affinity to MDM2 and was stable in solutions (FIG. 1). Unexpectedly, compounds No. 7 and No. 8 showed a much stronger antitumor activity than Compound No. 2 in mice bearing the SJSA-1 xenograft tumors. Specifically, Compounds No. 7 and No. 8 demonstrated complete and persistent tumor regression in mice bearing the SJSA-1 xenograft tumors (FIG. 2B).

Provided herein therefore are compounds of structural formula (I) that inhibit the interaction between p53 or p53-related proteins and MDM2 or MDM2-related proteins. By inhibiting the negative effect of MDM2 or MDM2-related proteins on p53 or p53-related proteins, the present compounds sensitize cells to inducers of apoptosis and/or cell cycle arrest. In one embodiment, the present compounds induce apoptosis and/or cell cycle arrest. Therefore, also provided herein are methods of sensitizing cells to inducers of apoptosis and/or cell cycle arrest and to methods of inducing apoptosis and/or cell cycle arrest in cells. The methods comprise contacting the cells with one or more compounds having a structural formula (I) either alone or in combination with additional agent(s), e.g., an inducer of apoptosis or a cell cycle disrupter.

The term "MDM2-related protein," as used herein, refers to proteins that have at least 25% sequence homology with MDM2, and interact with and inhibit p53 or p53-related proteins. Examples of MDM2-related proteins include, but are not limited to, MDMX.

The term "functional p53," as used herein, refers to wild-type p53 expressed at normal, high, or low levels and mutant or allelic variants of p53 that retain(s) at least about 5% of the activity of wild-type p53, e.g., at least about 10%, about 20%, about 30%, about 40%, about 50%, or more of wild-type activity.

The term "p53-related protein," as used herein, refers to proteins that have at least 25% sequence homology with p53, have tumor suppressor activity, and are inhibited by interaction with MDM2 or MDM2-related proteins. Examples of p53-related proteins include, but are not limited to, p63 and p73.

The term "disease" or "condition" denotes disturbances and/or anomalies that as a rule are regarded as being pathological conditions or functions, and that can manifest themselves in the form of particular signs, symptoms, and/or malfunctions. As demonstrated below, a compound of structural formula (I) is a potent inhibitor of an interaction between p53 and p53-related proteins and MDM2 and MDM2-related proteins and can be used in treating diseases and conditions wherein such inhibition provides a benefit.

The term "a disease or condition wherein inhibition of MDM2 or MDM2-related proteins provides a benefit" pertains to a condition in which inhibiting the interaction between p53 or p53-related proteins and MDM2 and MDM2-related proteins is important or necessary, e.g., for the onset, progress, expression of that disease or condition, or a disease or a condition which is known to be treated by MDM2 or MDM2-related protein inhibitor. Examples of such conditions include, but are not limited to, a cancer. One of ordinary skill in the art is readily able to determine whether a compound treats a disease or condition mediated by a MDM2 or an MDM2-related protein, for any particular cell type, for example, by assays which conveniently can be used to assess the activity of particular compounds.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas, leukemias, and the like. A neoplasm is said to be benign if it does not undergo invasion or metastasis, and malignant if it does either of these. A "metastatic" cell means that the cell can invade neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "senescence" as used herein, refers to the phenomenon whereby non-cancerous diploid cells lose the ability to divide, and characterized in part by telomeric dysfunction or shortening.

The terms "sensitize" and "sensitizing," as used herein, refer to making, through the administration of a first therapeutic agent (e.g., a compound provided herein), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second therapeutic agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The term "apoptosis-modulating agents," as used herein, refers to agents which are involved in modulating (e.g., inhibiting, decreasing, increasing, promoting) apoptosis. Examples of apoptosis-modulating agents include proteins which comprise a death domain such as, but not limited to, Fas/CD95, TRAMP, TNF RI, DR1, DR2, DR3, DR4, DR5, DR6, FADD, and RIP. Other examples of apoptosis-modulating agents include, but are not limited to, TNFα, Fas ligand, antibodies to Fas/CD95 and other TNF family receptors, TRAIL (also known as Apo2 Ligand or Apo2L/TRAIL), antibodies to TRAIL-R1 or TRAIL-R2, Bcl-2, p53, BAX, BAD, Akt, CAD, PI3 kinase, PP1, and caspase proteins. Modulating agents broadly include agonists and antagonists of TNF family receptors and TNF family ligands. Apoptosis-modulating agents may be soluble or membrane bound (e.g. ligand or receptor). Apoptosis-modulating agents include those which are inducers of apoptosis, such as TNF or a TNF-related ligand, particularly a TRAMP ligand, a Fas/CD95 ligand, a TNFR-1 ligand, or TRAIL.

The term "second therapeutic agent" refers to a therapeutic agent different from an MDM2 inhibitor of structural formula (I) and that is known to treat the disease or condition of interest. For example when a cancer is the disease or condition of interest, the second therapeutic agent can be an anticancer agent.

The term "anticancer agent" as used herein, refers to any therapeutic agent (e.g., chemotherapeutic compound and/or molecular therapeutic compound), antisense therapy, radiation therapy, or surgical intervention, used in the treatment of hyperproliferative diseases, such as cancer (e.g., in mammals, and particularly in humans).

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is (are) sufficient, when administered by a method of the invention, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce MDM2 and MDM2-related protein interactions with p53 and p53-related proteins; and/or relieve, to some extent, one or more of the symptoms associated with the cancer by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. To the extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, an MDM2 inhibitor of structural formula (I) can be administered at the same time or sequentially in any order at different points in time as a second therapeutic agent. A present MDM2 inhibitor and the second therapeutic agent can be administered separately, in any appropriate form and by any suitable route. When a present MDM2 inhibitor and the second therapeutic agent are not administered concurrently, it is understood that they can be administered in any order to a subject in need thereof. For example, a present MDM2 inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, an MDM2 inhibitor of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The terms "pulsatile administration," "pulsatile dose administration" or "pulsatile dosing" as used herein, refer to intermittent (i.e., not continuous) administration of compounds of structural formula (I) to a patient. Pulsatile dose administration regimens useful in the present disclosure encompass any discontinuous administration regimen that provides a therapeutically effective amount of compounds of structural formula (I) to a patient in need thereof. Pulsatile dosing regimens can use equivalent, lower, or higher doses of compounds of structural formula (I) than would be used in continuous dosing regimens. Advantages of pulsatile dose administration of compounds of structural formula (I) include, but are not limited to, improved safety, decreased toxicity, increased exposure, increased efficacy, and increased patient compliance. These advantages may be realized when compounds of structural formula (I) are administered as a single agent or are administered in combination with one or more additional anticancer agents. On the day that a compound of structural formula (I) is scheduled to be administered to the patient, administration can occur in a single or in divided doses, e.g., once-a-day, twice-a-day, three times a day, four times a day or more. In one embodiment, a compound having of structural formula (I) is administered once (QD) or twice (BID) on the day it is schedule to be administered.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

Research has established that targeting the p53-MDM2 interaction using small molecule inhibitors is a viable cancer therapeutic strategy. The prior discovery of MDM2 inhibitors and early data have demonstrated that non-peptide, small molecule inhibitors of MDM2-p53 interactions have great therapeutic potential for the treatment of diseases and conditions in which MDM2 and MDM2-related proteins have a role.

The present invention is directed to a new class of potent and specific inhibitors of MDM2-p53 interactions. The present compounds function as potent antagonists of MDM2-p53 interactions. The MDM2 inhibitors of the present invention therefore are useful in the treatment of a variety of diseases and conditions, including cancers, in subjects in need of such treatment. Also provided are methods of treating a subject having unwanted hyperproliferative cells comprising administering a therapeutically effective amount of a present compound to a subject in need of such treatment. Also provided are methods of preventing the proliferation of unwanted proliferating cells, such as cancers, in a subject comprising the step of administering a therapeutically effective amount of a compound of structural formula (I) to a subject at risk of developing a condition characterized by unwanted proliferating cells.

The present invention is directed to MDM2 inhibitors having a structural formula (I):

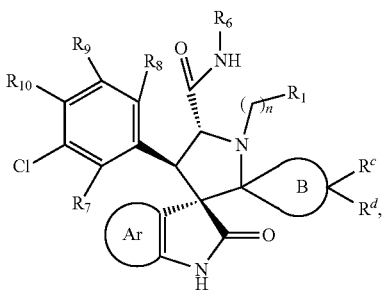

wherein

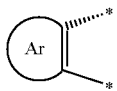

is selected from the group consisting of

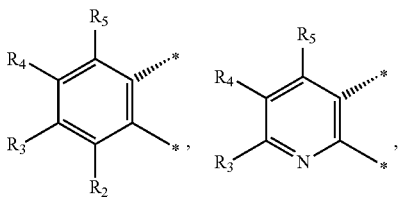

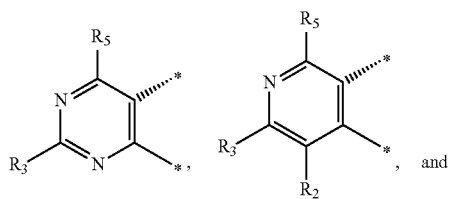

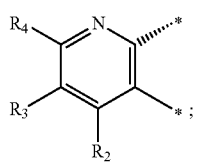

B is a $C_{4-7}$ carbocyclic ring;

$R_1$ is H, substituted or unsubstituted $C_{1-4}$alkyl, substituted or unsubstituted cycloalkyl, substituted or unsubstituted heterocycloalkyl, $OR^a$, or $NR^aR^b$;

n is 0, 1, or 2;

$R_2$, $R_3$, $R_4$, $R_5$, $R_7$, $R_8$, $R_9$, and $R_{10}$, independently, are selected from the group consisting of H, F, Cl, $CH_3$, and $CF_3$;

$R_6$ is

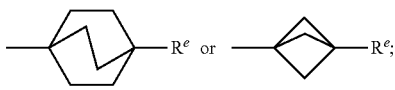

$R^a$ is hydrogen or substituted or unsubstituted $C_{1-4}$alkyl;
$R^b$ is hydrogen or substituted or unsubstituted $C_{1-4}$alkyl;
$R^c$ and $R^d$ are substituents on one carbon atom of ring B, wherein
$R^c$ is H, $C_{1-3}$alkyl, $C_{1-3}$alkyleneOR$^a$, OR$^a$, or halo;
$R^d$ is H, $C_{1-3}$alkyl, $C_{1-3}$alkyleneOR$^a$, OR$^a$, or halo; or
$R^c$ and $R^d$ are taken together with the carbon to which they are attached to form a 4 to 6-membered Spiro substituent, optionally containing an oxygen atom; and
$R^e$ is —C(=O)OR$^a$, —C(=O)NR$^a$R$^b$, or —C(=O)NHSO$_2$CH$_3$, or
a pharmaceutically acceptable salt thereof.

The compounds of structural formula (I) inhibit MDM2-p53 interactions and are useful in the treatment of a variety of diseases and conditions. In particular, the compounds of structural formula (I) are used in methods of treating a disease or condition wherein inhibition of MDM2 and MDM2-related protein provides a benefit, for example, cancers and proliferative diseases. The method comprises administering a therapeutically effective amount of a compound of structural formula (I) to an individual in need thereof. The present methods also encompass administering a second therapeutic agent to the individual in addition to the compound of structural formula (I). The second therapeutic agent is selected from drugs known as useful in treating the disease or condition afflicting the individual in need thereof, e.g., an anticancer agent known as useful in treating a particular cancer.

As used herein, the term "alkyl" refers to straight chained and branched saturated $C_{1-10}$ hydrocarbon groups, including but not limited to methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethylbutyl. The term $C_{m-n}$ means the alkyl group has "m" to "n" carbon atoms. The term "alkylene" refers to an alkyl group having a substituent. An alkyl, e.g., methyl, or alkylene, e.g., —CH$_2$—, group can be substituted with one or more, and typically one to three, of independently selected halo, trifluoromethyl, trifluoromethoxy, hydroxy, alkoxy, nitro, cyano, alkylamino, or amino groups, for example.

As used herein, the term "halo" is defined as fluoro, chloro, bromo, and iodo.

The term "hydroxy" is defined as —OH.

The term "alkoxy" is defined as —OR, wherein R is alkyl.

The term "amino" is defined as —NH$_2$, and the term "alkylamino" is defined as —NR$_2$, wherein at least one R is alkyl and the second R is alkyl or hydrogen.

The term "carbamoyl" is defined as —C(=O)NR$_2$.

The term "carboxy" is defined as —C(=O)OH or a salt thereof.

The term "nitro" is defined as —NO$_2$.

The term "cyano" is defined as —CN.

The term "trifluoromethyl" is defined as —CF$_3$.

The term "trifluoromethoxy" is defined as —OCF$_3$.

As used herein, groups such as

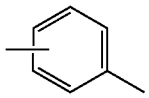

is an abbreviation for

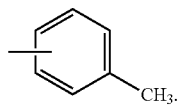

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "heterocyclic" refers to a heteroaryl and heterocycloalkyl ring systems.

As used herein, the term "heteroaryl" refers to a monocyclic or bicyclic ring system containing one or two aromatic rings and containing at least one nitrogen, oxygen, or sulfur atom in an aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl group has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four, substituents selected from, for example, halo, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "cycloalkyl" means a monocyclic or bicyclic, saturated or partially unsaturated, ring system containing three to eight carbon atoms, including cyclopropyl, cyclobutyl, cyclopentyl, cyclohexyl, cycloheptyl, and cyclooctyl, optionally substituted with one or more, and typically one to three, of independently selected halo, trifluoromethyl, trifluoromethoxy, hydroxy, alkoxy, nitro, cyano, alkylamino, or amino groups, for example.

As used herein, the term "heterocycloalkyl" means a monocyclic or a bicyclic, saturated or partially unsaturated, ring system containing 4 to 12 total atoms, of which one to five of the atoms are independently selected from nitrogen, oxygen, and sulfur and the remaining atoms are carbon. Nonlimiting examples of heterocycloalkyl groups are azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, diazacycloheptyl, each optionally substituted with one or more, and typically one to three, of independently selected halo, $C_{1-6}$ alkyl, $C_{1-6}$ alkoxy, cyano, amino, carbamoyl, nitro, carboxy, $C_{2-7}$ alkenyl, $C_{2-7}$ alkynyl, or the like on an atom of the ring.

In some preferred embodiments,

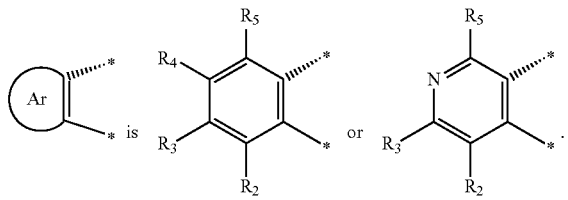

In other embodiments, B is

In various embodiments, n is 0 or 1 and $R_1$ is H or $CH_3$. In various embodiments, —(CH$_2$)$_n$—R$_1$ is H, CH$_3$, or CH$_2$CH$_3$.

In various embodiments, $R_2$ is H. In other embodiments, $R_3$ is halo, and preferably chloro. In still another embodiments, $R_4$ is H, $R_5$ is H, or both $R_4$ and $R_5$ are H.

In some preferred embodiments, $R_7$ is halo, and more preferably is fluoro.

In some embodiments, each of $R^8$, $R^9$, and $R^{10}$ are H.

In various embodiments, $R^a$ and $R^b$, individually, are H, CH$_3$, or CH$_2$CH$_3$.

In other embodiments, $R^c$ and $R^d$, individually, are H, halo, OH, CH$_3$, CH$_2$CH$_3$, or CH$_2$OH. In some embodiments, $R^c$ and $R^d$ are F and F, H and H, OH and CH$_3$, CH$_3$ and CH$_3$, CH$_3$ and OH, H and OH, CH$_2$CH$_3$ and CH$_2$CH$_3$, and CH$_2$OH and CH$_2$OH.

In other embodiments, $R^c$ and $R^d$ are taken together with ring B to form a spiro moiety, for example

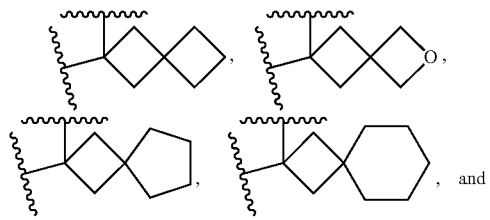

-continued

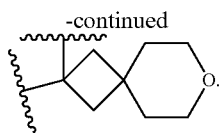

In other embodiments, $R^c$ and $R^d$ taken with ring B form:

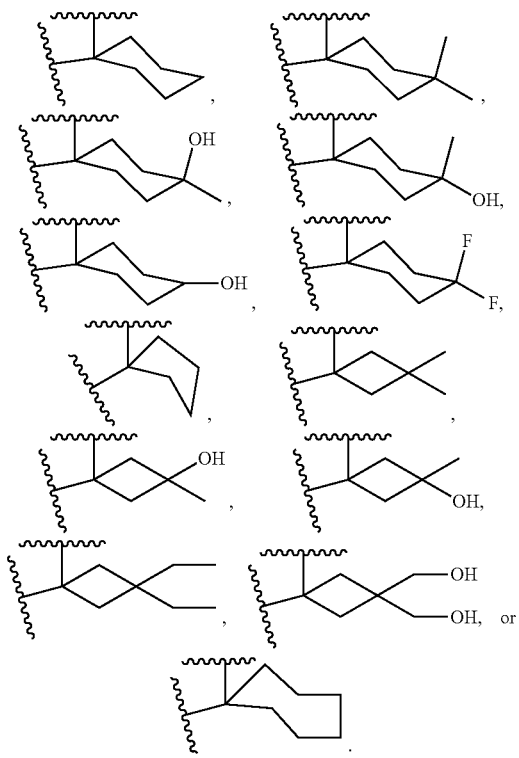

In some embodiments, $R^e$ is —C(=O)OH, —C(=O)NH$_2$, or —C(=O)NHSO$_2$CH$_3$.

In various embodiments, $R^6$ is

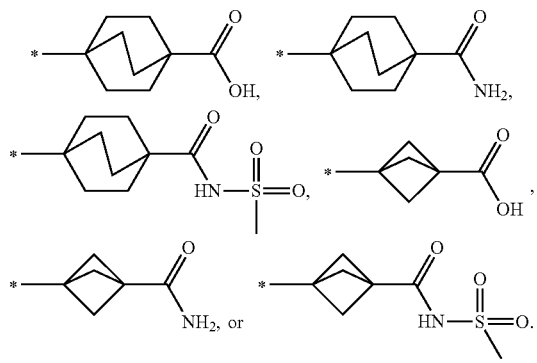

Additionally, salts of the present compounds also are included in the present invention and can be used in the methods disclosed herein. The present invention further includes all possible stereoisomers and geometric isomers of the compounds of structural formula (I). The present invention includes both racemic compounds and optically active isomers. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

Certain of the compounds of the present disclosure may exist as stereoisomers, i.e., isomers that differ only in the spatial arrangement of atoms, including optical isomers and conformational isomers (or conformers). The disclosure includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

The term "substantially free of" as used herein means that the compound comprises less than about 25% of other stereoisomers, e.g., diastereomers and/or enantiomers, as established using conventional analytical methods routinely used by those of skill in the art. In one embodiment, the amount of other stereoisomers is less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less than about 0.5%.

Stereoisomerically enriched compounds that contain about 95% or more of a desired stereoisomer, for example, about 96% or more, about 97% or more, about 98% or more, or about 99% or more are referred to herein as "substantially pure stereoisomers."

Stereoisomerically enriched compounds that contain about 99% or more of a desired stereoisomer are referred to herein as "pure" stereoisomers." The purity of any stereoisomerically enriched compound can be determined using conventional analytical methods such as, for example, normal phase HPLC, reverse phase HPLC, chiral HPLC, and $^1$H and $^{13}$C NMR.

Compounds of the invention can exist as salts. Pharmaceutically acceptable salts of the compounds of the invention often are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid having a suitable cation, such as, but not limited to, alkali and alkaline earth metal ions, e.g., Na$^+$, K$^+$, Ca$^{2+}$, and Mg$^{2+}$ well as organic cations such as, but not limited to, ammonium and substituted ammonium ions, e.g., NH$_4^+$, NHMe$_3^+$, NH$_2$Me$_2^+$, NHMe$_3^+$ and NMe$_4^+$. Examples of monovalent and divalent pharmaceutically acceptable cations are discussed, e.g., in Berge et al. *J. Pharm. Sci.*, 66:1-19 (1997).

The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I) as well as pharmaceutically acceptable salts thereof.

Specific compounds of the present invention include, but are not limited to, compounds having the structure set forth below.

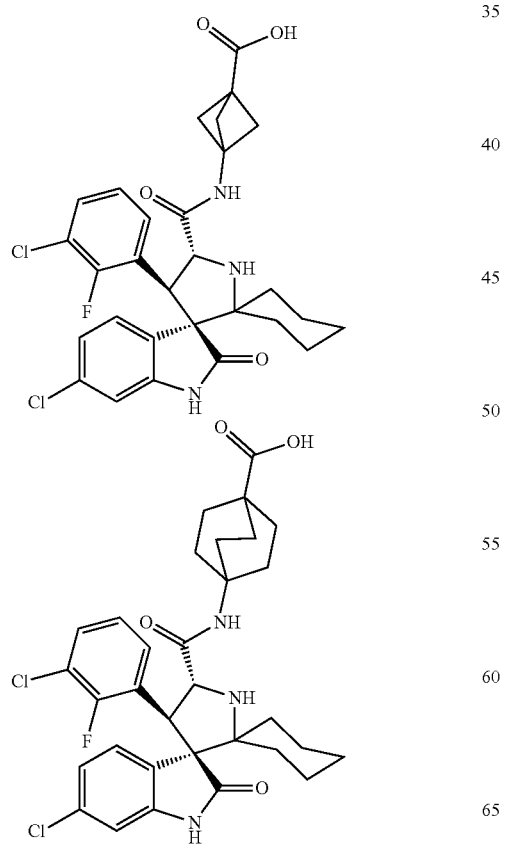

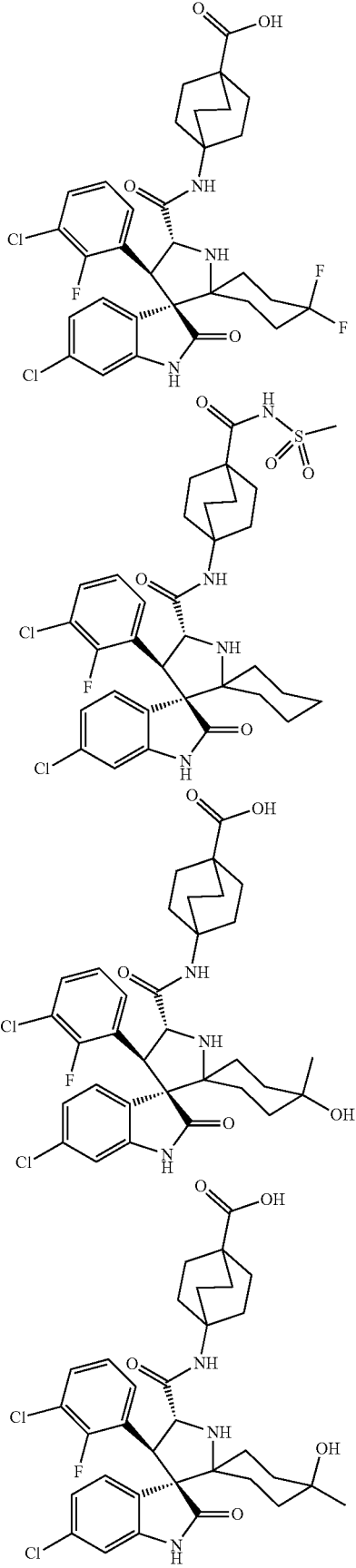

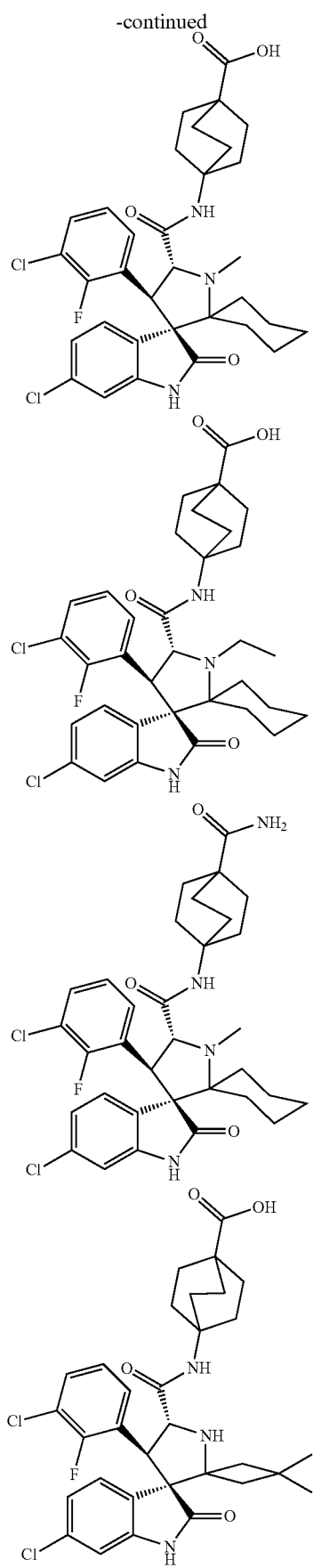
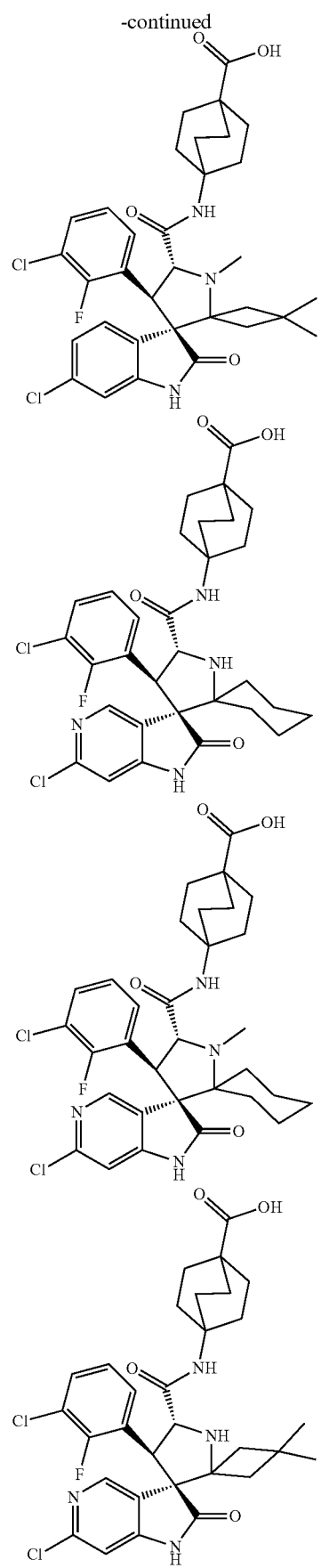

-continued

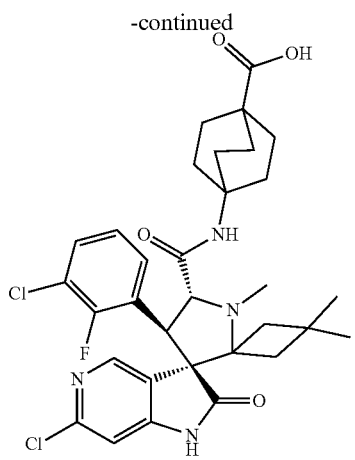

The present invention provides MDM2 inhibitors, as exemplified by compounds of structural formula (I), for the treatment of a variety of diseases and conditions wherein inhibition of MDM2 and MDM-2 related proteins has a beneficial effect. In one embodiment, the present invention relates to a method of treating an individual suffering from a disease or condition wherein inhibition of the MDM2 and MDM2-related proteins provides a benefit comprising administering a therapeutically effective amount of a compound of structural formula (I) to an individual in need thereof.

The present methods contemplate that exposure of animals or patients suffering from cancer to therapeutically effective amounts of drug(s) (e.g., small molecules) that increase the function(s) of p53 and p53-related proteins (e.g., p63, p73) inhibits the growth of cancer cells or supporting cells. The present MDM2 inhibitors provided herein inhibit the interaction between p53 or p53-related proteins and MDM2 or MDM2-related proteins (e.g., MDMX). Inhibiting the interaction between p53 or p53-related proteins and MDM2 or MDM2-related proteins inhibits the growth of cancer cells or supporting cells and/or renders such cells as a population more susceptible to the cell death-inducing activity of cancer therapeutic drugs or radiation therapies. In one embodiment, the MDM2 inhibitors provided herein prolong the half-life of p53 by interfering with the p53-MDM2 interaction that would normally promote degradation of p53. The compounds provided herein satisfy an unmet need for the treatment of multiple cancer types, either when administered as monotherapy to induce senescence, cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal or a patient treated only with the cancer therapeutic drug or radiation therapy alone.

In one embodiment, treatment of patients with a therapeutically effective amount of one or more compounds of structural formula (I) and one or more anticancer agents produces a greater anti-tumor activity and clinical benefit in such patients compared to those treated with the compound or anticancer drugs/radiation alone. Alternately stated, because the present compounds lower the apoptotic threshold of cells that express p53 or p53-related protein, the proportion of cells that successfully execute the apoptosis program in response to the apoptosis inducing activity of anticancer drugs/radiation will be increased when used in combination with one or more of the present compounds. Compounds of structural formula (I) therefore can be used to allow administration of a lower, and therefore less toxic and more tolerable, dose of an anticancer drug and/or radiation to produce the same tumor response/clinical benefit as the conventional dose of the anticancer drug/radiation alone. Because the doses for approved anticancer drugs and radiation treatments are known, the compounds, compositions, and methods provided herein can be used with one or more approved anticancer drugs and/or radiation treatment. Also, because compounds of structural formula (I) can act, at least in part, by stimulating the pro-apoptotic and/or cell cycle-inhibiting activities of p53 and p53-related proteins, the exposure of cancer cells and supporting cells to therapeutically effective amounts of these compounds can be temporally linked to coincide with the attempts of cells to execute the apoptosis program in response to the anticancer drug or radiation therapy. Thus, in one embodiment, administering the compounds or pharmaceutical compositions provided herein in combination with other known anticancer drugs provides especially efficacious therapeutic practices.

In one embodiment, the inhibitors of the interaction between p53 or p53-related proteins and MDM2 and MDM2-related proteins of structural formula (I) can protect normal (e.g., non-hyperproliferative) cells from the toxic effects of certain chemotherapeutic agents and radiation, possibly through the ability of the inhibitors to induce cell cycle arrest of normal cells. For example, the MDM2 inhibitors provided herein may cause cell cycle arrest in cells comprising wild-type or functional p53 (and/or wild-type or functional p53-related proteins) while having no or less effect on cancer cells comprising mutated, deleted, or otherwise non- or less functional p53 (and/or mutated, deleted, or otherwise non- or less functional p53-related proteins). This differential protective effect can allow for more effective treatment of cancer by allowing the use of higher doses or longer treatments of chemotherapeutic agents or treatments without increasing the toxic side effects of such treatment when administered in combination with inhibitors provided herein.

Also provided herein are methods of using compounds of structural formula (I) for sensitizing cells to additional agent(s), such as inducers of senescence, apoptosis, and/or cell cycle arrest. Compounds of structural formula (I) also can be used to provide chemoprotection of normal cells through the induction of cell cycle arrest prior to treatment with chemotherapeutic agents. In one embodiment, methods of rendering a normal cell resistant to chemotherapeutic agents or treatments comprises contacting the cell with one or more compounds of structural formula (I) are provided. In another embodiment, methods of protecting normal cells in an animal having a hyperproliferative disease from the toxic side effects of chemotherapeutic agents or treatments, comprises administering to the animal a compound of structural formula (I) are provided. Also provided herein are methods for the treatment, amelioration, or prevention of disorders, side effects, or conditions caused by the administration of chemotherapeutic agents to normal cells comprising administering to an animal undergoing chemotherapy a compound of structural formula (I). Examples of such disorders and conditions caused by chemotherapy include, without limitation, mucositis, stomatitis, xerostomia, gastrointestinal disorders, and alopecia.

Compounds of structural formula (I) are useful for the treatment, amelioration, or prevention of disorders, such as those responsive to induction of apoptotic cell death, e.g., disorders characterized by dysregulation of apoptosis, including hyperproliferative diseases such as cancer. In one embodiment, these compounds can be used to treat, or ameliorate cancer that is characterized by resistance to cancer therapies (e.g., those cancer cells which are chemoresistant, radiation resistant, hormone resistant, and the like). In another embodiment, the present compounds can be used to treat hyperproliferative diseases characterized by expression of functional p53 or p53-related proteins. In another embodiment, the present compounds can be used to protect normal (e.g., non-hyperproliferative) cells from the toxic side effects of chemotherapeutic agents and treatments by the induction of cell cycle arrest in those cells.

In one embodiment, compounds of structural formula (I) induce cell cycle arrest and/or apoptosis and also potentiate the induction of cell cycle arrest and/or apoptosis either alone or in response to additional apoptosis induction signals. Therefore, it is contemplated that the present compounds sensitize cells to induction of cell cycle arrest and/or apoptosis, including cells that are resistant to such inducing stimuli. By inhibiting the interaction between p53 or p53-related proteins and MDM2 or MDM2-related proteins, the present compounds can be used to induce apoptosis in any disorder that can be treated, ameliorated, or prevented by the induction of apoptosis. In one embodiment, compounds of structural formula (I) can be used to induce apoptosis in cells comprising functional p53 or p53-related proteins.

The compounds of structural formula (I), in combination with one or more additional apoptosis-modulating agents, e.g., anticancer agents, to modulate apoptosis. Examples of apoptosis-modulating agents include, but are not limited to, Fas/CD95, TRAMP, TNF RI, DR1, DR2, DR3, DR4, DR5, DR6, FADD, RIP, TNFα, Fas ligand, TRAIL, antibodies to TRAIL-R1 or TRAIL-R2, Bcl-2, p53, BAX, BAD, Akt, CAD, PI3 kinase, PP1, and caspase proteins. Other agents involved in the initiation, decision and degradation phase of apoptosis also are included. Examples of apoptosis-modulating agents include agents, the activity, presence, or change in concentration of which, can modulate apoptosis in a subject. Apoptosis-modulating agents include those which are inducers of apoptosis, such as TNF or a TNF-related ligand, particularly a TRAMP ligand, a Fas/CD95 ligand, a TNFR-1 ligand, or TRAIL.

The compounds, compositions, and methods herein are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A nonlimiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia (CLL) including B-CLL, acute myelogenous leukemia, chronic myelogenous leukemia, chronic granulocytic leukemia, acute granulocytic leukemia, hairy cell leukemia, neuroblastoma, sarcoma such as liposarcoma malignant fibrous histiocytoma, osteosarcoma, Ewing's sarcoma, leiomyosarcoma, and rhabdomyosarcoma, Kaposi's sarcoma, polycythemia vera, essential thrombocytosis, Hodgkin's disease, non-Hodgkin's lymphoma, soft-tissue sarcomas such as lipoma, and malignant Schwannoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In one embodiment, the cancer cells being treated are metastatic. In another embodiment, the cancer cells being treated are resistant to other anticancer agents.

The compounds, compositions, and methods herein are used to treat cancers that express functional or wild type p53 or p53-related proteins. In one embodiment, the compounds, compositions, and methods provided herein are used to treat cancers that express elevated levels of MDM2 or MDM2-related proteins.

The compounds, compositions, and methods herein can be used to treat a patient having a sarcoma, including, for example, liposarcoma, malignant fibrous histiocytoma, osteosarcoma, and rhabdomyosarcoma. In another embodiment, the compounds, compositions, and methods provided herein can be used to treat a patient having a soft tissue tumor, including, for example, Ewing's sarcoma, leiomyosarcoma, lipoma, and malignant Schwannomas. In another embodiment, the compounds, compositions, and methods provided herein can be used to treat a patient having lung, breast, liver, or colon cancer. In another embodiment, the compounds, compositions, and methods provided herein can be used to treat a patient having B-cell chronic lymphocytic leukemia and acute myeloid leukemia.

The compounds, compositions, and methods provided here also can be used to treat a patient having melanoma, lung cancer, sarcoma, colon cancer, prostate cancer, choriocarcinoma, breast cancer, retinoblastoma, stomach carcinoma, acute myeloid leukemia, lymphoma, multiple myeloma, or leukemia.

The compounds, compositions, and methods provided here further can be used to treat a patient having liposarcoma or melanoma.

Infections suitable for treatment using the compounds, compositions, and methods herein include, but are not limited to, infections caused by viruses, bacteria, fungi, *mycoplasma*, prions, and the like.

The present compounds of structural formula (I), or a pharmaceutical composition comprising a compound of structural formula (I), are useful in treating a hyperproliferative disease such as cancer.

The methods provided for administering an effective amount of a compound of structural formula (I) in combination with at least one second therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention and/or radiotherapies). In preferred embodiments, the second therapeutic agent(s) is an anticancer agent.

A number of second suitable therapeutic or anticancer agents are contemplated for use in the present methods. Indeed, the methods provided herein can include but are not limited to, administration of numerous therapeutic agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of therapeutic agents, such as chemotherapeutic compounds and anticancer therapies suitable for co-administration with the disclosed compounds, are known to those skilled in the art.

Anticancer agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor. Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethimide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTAS ONE, dexamethasone, dexamethasone intensol, DEX-ONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

The compositions and methods herein include one or more compounds of structural formula (I) and at least one antihyperproliferative or anticancer agent, e.g., alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

Antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

Chemotherapeutic agents suitable for use in the present compositions and methods include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any anticancer agent routinely used in a cancer therapy context finds use in the compositions and methods of the present invention. Table 1 provides a list of exemplary antineoplastic agents. Those skilled in the art appreciate that the "product labels" required on all U.S. approved chemotherapeutics describe approved indications, dosing information, toxicity data, and the like, for the exemplary agents.

TABLE 1

| | |
|---|---|
| Aldesleukin | Proleukin |
| (des-alanyl-1, serine-125 human interleukin-2) | |
| Alemtuzumab | Campath |
| (IgG1κ anti CD52 antibody) | |
| Alitretinoin | Panretin |
| (9-cis-retinoic acid) | |
| Allopurinol | Zyloprim |
| (1,5-dihydro-4H-pyrazolo[3,4-d]pyrimidin-4-one monosodium salt) | |

TABLE 1-continued

| | |
|---|---|
| Altretamine | Hexalen |
| (N,N,N',N',N'',N''-hexamethyl-1,3,5-triazine-2,4,6-triamine) | |
| Amifostine | Ethyol |
| (ethanethiol, 2-[(3-aminopropyl)amino]-, dihydrogen phosphate (ester)) | |
| Anastrozole | Arimidex |
| (1,3-Benzenediacetonitrile, a,a,a',a'-tetramethyl-5-(1H-1,2,4-triazol-1-ylmethyl)) | |
| Arsenic trioxide | Trisenox |
| Asparaginase | Elspar |
| (L-asparagine amidohydrolase, type EC-2) | |
| BCG Live | TICE BCG |
| (lyophilized preparation of an attenuated strain of *Mycobacterium bovis* (*Bacillus Calmette*-Gukin [BCG], substrain Montreal) | |
| bexarotene capsules | Targretin |
| (4-[1-(5,6,7,8-tetrahydro-3,5,5,8,8-pentamethyl-2-napthalenyl) ethenyl] benzoic acid) | |
| bexarotene gel | Targretin |
| Bleomycin | Blenoxane |
| (cytotoxic glycopeptide antibiotics produced by *Streptomyces verticillus*; bleomycin $A_2$ and bleomycin $B_2$) | |
| Capecitabine | Xeloda |
| (5'-deoxy-5-fluoro-N-[(pentyloxy)carbonyl]-cytidine) | |
| Carboplatin | Paraplatin |
| (platinum, diammine [1,1-cyclobutanedicarboxylato(2-)-0,0']-,(SP-4-2)) | |
| Carmustine | BCNU, BiCNU |
| (1,3-bis(2-chloroethyl)-1-nitrosourea) | |
| Carmustine with Polifeprosan 20 Implant | Gliadel Wafer |
| Celecoxib | Celebrex |
| (as 4-[5-(4-methylphenyl)-3-(trifluoromethyl)-1H-pyrazol-1-yl] benzenesulfonamide) | |
| Chlorambucil | Leukeran |
| (4-[bis(2chlorethyl)amino]benzenebutanoic acid) | |
| Cisplatin | Platinol |
| ($PtCl_2H_6N_2$) | |
| Cladribine | Leustatin, 2-CdA |
| (2-chloro-2'-deoxy-b-D-adenosine) | |
| Cyclophosphamide | Cytoxan, Neosar |
| (2-[bis(2-chloroethyl)amino] tetrahydro-2H-13,2-oxazaphosphorine 2-oxide monohydrate) | |
| Cytarabine | Cytosar-U |
| (1-b-D-Arabinofuranosylcytosine, $C_9H_{13}N_3O_5$) | |
| cytarabine liposomal | DepoCyt |
| Dacarbazine | DTIC-Dome |
| (5-(3,3-dimethyl-1-triazeno)-imidazole-4-carboxamide (DTIC)) | |
| Dactinomycin, actinomycin D | Cosmegen |
| (actinomycin produced by *Streptomyces parvullus*, $C_{62}H_{86}N_{12}O_{16}$) | |
| Darbepoetin alfa | Aranesp |
| (recombinant peptide) | |
| daunorubicin liposomal | DanuoXome |
| ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | |
| Daunorubicin HCl, daunomycin | Cerubidine |
| ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | |
| Denileukin diftitox | Ontak |
| (recombinant peptide) | |
| Dexrazoxane | Zinecard |
| ((S)-4,4'-(1-methyl-1,2-ethanediyl)bis-2,6-piperazinedione) | |
| Docetaxel | Taxotere |
| ((2R,3S)—N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | |
| Doxorubicin HCl | Adriamycin, Rubex |
| (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | |
| doxorubicin | Adriamycin PFS Intravenous injection |
| doxorubicin liposomal | Doxil |
| dromostanolone propionate | Dromostanolone |
| (17b-Hydroxy-2a-methyl-5a-androstan-3-one propionate) | |
| dromostanolone propionate | Masterone injection |
| Elliott's B Solution | Elliott's B Solution |
| Epirubicin | Ellence |
| ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | |
| Epoetin alfa | Epogen |
| (recombinant peptide) | |
| Estramustine | Emcyt |
| (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | |

TABLE 1-continued

| | |
|---|---|
| Etoposide phosphate<br>(4'-Demethylepipodophyllotoxin 9-[4,6-O-(R)-ethylidene-(beta)-D-glucopyranoside], 4'-(dihydrogen phosphate)) | Etopophos |
| etoposide, VP-16<br>(4'-demethylepipodophyllotoxin 9-[4,6-0-(R)-ethylidene-(beta)-D-glucopyranoside]) | Vepesid |
| Exemestane<br>(6-methylenandrosta-1,4-diene-3,17-dione) | Aromasin |
| Filgrastim<br>(r-metHuG-CSF) | Neupogen |
| floxuridine (intraarterial)<br>(2'-deoxy-5-fluorouridine) | FUDR |
| Fludarabine<br>(fluorinated nucleotide analog of the antiviral agent vidarabine, 9-b-D-arabinofuranosyladenine (ara-A)) | Fludara |
| Fluorouracil, 5-FU<br>(5-fluoro-2,4(1H,3H)-pyrimidinedione) | Adrucil |
| Fulvestrant<br>(7-alpha-[9-(4,4,5,5,5-penta fluoropentylsulphinyl) nonyl]estra-1,3,5-(10)-triene-3,17-beta-diol) | Faslodex |
| Gemcitabine<br>(2'-deoxy-2',2'-difluorocytidine monohydrochloride (b-isomer)) | Gemzar |
| Gemtuzumab Ozogamicin<br>(anti-CD33 hP67.6) | Mylotarg |
| Goserelin acetate | Zoladex Implant |
| Hydroxyurea | Hydrea |
| Ibritumomab Tiuxetan<br>(immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino-2-(methyl)-ethyl]glycine) | Zevalin |
| Idarubicin<br>(5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin |
| Ifosfamide<br>(3-(2-chloroethyl)-2-[(2-chloroethyl)amino]tetrahydro-2H-1,3,2-oxazaphosphorine 2-oxide) | IFEX |
| Imatinib Mesilate<br>(4-[(4-Methyl-1-piperazinyl)methyl]-N-[4-methyl-3-[[4-(3-pyridinyl)-2-pyrimidinyl]amino]-phenyl]benzamide methanesulfonate) | Gleevec |
| Interferon alfa-2a<br>(recombinant peptide) | Roferon-A |
| Interferon alfa-2b<br>(recombinant peptide) | Intron A (Lyophilized Betaseron) |
| Irinotecan HCl<br>((4S)-4,11-diethyl-4-hydroxy-9-[(4-piperidinopiperidino)carbonyloxy]-1H-pyrano[3',4':6,7] indolizino[1,2-b] quinoline-3,14(4H,12H) dione hydrochloride trihydrate) | Camptosar |
| Letrozole<br>(4,4'-(1H-1,2,4-Triazol-1-ylmethylene) dibenzonitrile) | Femara |
| Leucovorin<br>(L-Glutamic acid, N[4[[(2amino-5-formyl1,4,5,6,7,8 hexahydro4oxo6-pteridinyl)methyl]amino]benzoyl], calcium salt (1:1)) | Wellcovorin,<br>Leucovorin |
| Levamisole HCl<br>((−)-(S)-2,3,5,6-tetrahydro-6-phenylimidazo [2,1-b] thiazole monohydrochloride $C_{11}H_{12}N_2S \bullet HCl$) | Ergamisol |
| Lomustine<br>(1-(2-chloro-ethyl)-3-cyclohexyl-1-nitrosourea) | CeeNU |
| Meclorethamine, nitrogen mustard<br>(2-chloro-N-(2-chloroethyl)-N-methylethanamine hydrochloride) | Mustargen |
| Megestrol acetate<br>17α(acetyloxy)-6-methylpregna-4,6-diene-3,20-dione | Megace |
| Melphalan, L-PAM<br>(4-[bis(2-chloroethyl) amino]-L-phenylalanine) | Alkeran |
| Mercaptopurine, 6-MP<br>(1,7-dihydro-6H-purine-6-thione monohydrate) | Purinethol |
| Mesna<br>(sodium 2-mercaptoethane sulfonate) | Mesnex |
| Methotrexate<br>(N-[4-[[(2,4-diamino-6-pteridinyl)methyl]methylamino]benzoyl]-L-glutamic acid) | Methotrexate |
| Methoxsalen<br>(9-methoxy-7H-furo[3,2-g][1]-benzopyran-7-one) | Uvadex |
| Mitomycin C | Mutamycin |
| mitomycin C | Mitozytrex |
| Mitotane<br>(1,1-dichloro-2-(o-chlorophenyl)-2-(p-chlorophenyl) ethane) | Lysodren |
| Mitoxantrone<br>(1,4-dihydroxy-5,8-bis[[2-[(2-hydroxyethyl)amino]ethyl]amino]-9,10-anthracenedione dihydrochloride) | Novantrone |

TABLE 1-continued

| | |
|---|---|
| Nandrolone phenpropionate | Durabolin-50 |
| Nofetumomab | Verluma |
| Oprelvekin | Neumega |
| (IL-11) | |
| Oxaliplatin | Eloxatin |
| (cis-[(1R,2R)-1,2-cyclohexanediamine-N,N'] [oxalato(2-)-O,O'] platinum) | |
| Paclitaxel | TAXOL |
| (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | |
| Pamidronate | Aredia |
| (phosphonic acid (3-amino-1-hydroxypropylidene) bis-, disodium salt, pentahydrate, (APD)) | |
| Pegademase | Adagen (Pegademase Bovine) |
| ((monomethoxypolyethylene glycol succinimidyl) 11-17-adenosine deaminase) | |
| Pegaspargase | Oncaspar |
| (monomethoxypolyethylene glycol succinimidyl L-asparaginase) | |
| Pegfilgrastim | Neulasta |
| (covalent conjugate of recombinant methionyl human G-CSF (Filgrastim) and monomethoxypolyethylene glycol) | |
| Pentostatin | Nipent |
| Pipobroman | Vercyte |
| Plicamycin, Mithramycin | Mithracin |
| (antibiotic produced by *Streptomyces plicatus*) | |
| Porfimer sodium | Photofrin |
| Procarbazine | Matulane |
| (N-isopropyl-μ-(2-methylhydrazino)-p-toluamide monohydrochloride) | |
| Quinacrine | Atabrine |
| (6-chloro-9-(1-methyl-4-diethyl-amine) butylamino-2-methoxyacridine) | |
| Rasburicase | Elitek |
| (recombinant peptide) | |
| Rituximab | Rituxan |
| (recombinant anti-CD20 antibody) | |
| Sargramostim | Prokine |
| (recombinant peptide) | |
| Streptozocin | Zanosar |
| (streptozocin 2-deoxy-2-[[(methylnitrosoamino)carbonyl]amino]-a(and b)-D-glucopyranose and 220 mg citric acid anhydrous) | |
| Talc | Sclerosol |
| $(Mg_3Si_4O_{10}(OH)_2)$ | |
| Tamoxifen | Nolvadex |
| ((Z)2-[4-(1,2-diphenyl-1-butenyl) phenoxy]-N,N-dimethylethanamine 2-hydroxy-1,2,3-propanetricarboxylate (1:1)) | |
| Temozolomide | Temodar |
| (3,4-dihydro-3-methyl-4-oxoimidazo[5,1-d]-as-tetrazine-8-carboxamide) | |
| teniposide, VM-26 | Vumon |
| (4'-demethylepipodophyllotoxin 9-[4,6-0-(R)-2-thenylidene-(beta)-D-glucopyranoside]) | |
| Testolactone | Teslac |
| (13-hydroxy-3-oxo-13,17-secoandrosta-1,4-dien-17-oic acid [dgr]-lactone) | |
| Thioguanine, 6-TG | Thioguanine |
| (2-amino-1,7-dihydro-6H-purine-6-thione) | |
| Thiotepa | Thioplex |
| (Aziridine, 1,1',1''-phosphinothioylidynetris-, or Tris (1-aziridinyl) phosphine sulfide) | |
| Topotecan HCl | Hycamtin |
| ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | |
| Toremifene | Fareston |
| (2-(p-[(Z)-4-chloro-1,2-diphenyl-1-butenyl]-phenoxy)-N,N-dimethylethylamine citrate (1:1)) | |
| Tositumomab, I 131 Tositumomab | Bexxar |
| (recombinant murine immunotherapeutic monoclonal $IgG_{2a}$ lambda anti-CD20 antibody (I 131 is a radioimmunotherapeutic antibody)) | |
| Trastuzumab | Herceptin |
| (recombinant monoclonal $IgG_1$ kappa anti-HER2 antibody) | |
| Tretinoin, ATRA | Vesanoid |
| (all-trans retinoic acid) | |
| Uracil Mustard | Uracil Mustard Capsules |
| Valrubicin, N-trifluoroacetyladriamycin-14-valerate | Valstar |
| ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | |
| Vinblastine, Leurocristine | Velban |
| $(C_{46}H_{56}N_4O_{10} \cdot H_2SO_4)$ | |
| Vincristine | Oncovin |
| $(C_{46}H_{56}N_4O_{10} \cdot H_2SO_4)$ | |

TABLE 1-continued

| | |
|---|---|
| Vinorelbine (3',4'-didehydro-4'-deoxy-C'-norvincaleukoblastine [R-(R*,R*)-2,3-dihydroxybutanedioate (1:2)(salt)]) | Navelbine |
| Zoledronate, Zoledronic acid ((1-Hydroxy-2-imidazol-1-yl-phosphonoethyl) phosphonic acid monohydrate) | Zometa |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675, 206, CP-724, 714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The methods provided herein comprise administering one or more compounds of structural formula (I) in combination with radiation therapy. The methods provided herein are not limited by the types, amounts, or delivery and administration systems used to deliver the therapeutic dose of radiation to an animal. For example, the mammal can receive photon radiotherapy, particle beam radiation therapy, other types of radiotherapies, and combinations thereof. In one embodiment, the radiation is delivered to the animal using a linear accelerator. In another embodiment, the radiation is delivered using a gamma knife.

The source of radiation can be external or internal to the mammal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by mammal. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The mammal optionally can receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tirapazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to the mammal, is long as the dose of radiation is tolerated by the mammal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the mammal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the responsiveness of the mammal and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the methods provided herein.

Antimicrobial therapeutic agents may also be used as therapeutic agents in combination with the compounds of structural formula (I). Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In the present methods, one or more compounds of structural formula (I) are administered to a mammal in need thereof. In another embodiment of the methods, one or more compound and one or more second therapeutic agents, i.e., as anticancer agents, are administered to a mammal in need thereof under one or more of the following conditions: for example, at different periodicities, at different durations, at different concentrations, by different administration routes. In one embodiment, the compound of structural formula (I) is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the second therapeutic or anticancer agent. In another embodiment, the compound of structural formula (I) is administered after the second therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In another embodiment, the compound of structural formula (I) and the second therapeutic or anticancer agent are administered concurrently, but on different schedules, e.g., the compound is administered daily while the second therapeutic or anticancer agent is administered once a week, once every two weeks, once every three weeks, or once every four weeks. In another embodiment, a present compound is administered once a week and the second therapeutic or anticancer agent is administered daily, once a week, once every two weeks, once every three weeks, or once every four weeks.

In one embodiment, a method of treating, or ameliorating cancer in a patient comprises a pulsatile administration of a therapeutically effective amount of a compound of structural formula (I) to the patient.

Toxicity and therapeutic efficacy of the compounds of structural formula (I) can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I) required for use in therapy varies with the nature of the condition being treated, the length of time that activity is desired, and the age and the condition of the patient, and ultimately is determined by the attendant physician. Dosage amounts and intervals can be adjusted individually to provide plasma levels of the MDM2 inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present MDM2 inhibitor can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The pharmaceutical compositions provided herein comprise one or more compounds of structural formula (I) in an amount effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat or ameliorate disorders. For intramuscular injection, the dose is generally about one-half of the oral dose. For example, a suitable intramuscular dose is about 0.0025 to about 25 mg/kg, or from about 0.01 to about 5 mg/kg.

The unit oral dose can comprise from about 1 to about 2000 mg, for example, about 100 to about 1000 mg of a present compound. The unit dose can be administered one or more times daily as one or more tablets or capsules each containing from about 5 to about 500 mg, conveniently about 50 to 250 mg of the compound or its salts.

In a topical formulation, the compound can be present at a concentration of about 0.01 to 100 mg per gram of carrier. In a one embodiment, the compound is present at a concentration of about 5-100 mg/ml.

In addition to administering the compound as a heat chemical, compounds of structural formula (I) can be administered as a component of a pharmaceutical preparation or composition. The pharmaceutical composition comprises one or more pharmaceutically acceptable carriers, excipients, and/or auxiliaries. The one or more carriers, excipients, and auxiliaries facilitate processing of a compound of structural formula (I) into a preparation which can be used pharmaceutically. The compositions, particularly compositions that can be administered orally or topically that can be used for one type of administration, such as tablets, dragees, slow release lozenges and capsules, mouth rinses and mouth washes, gels, liquid suspensions, hair rinses, hair gels, shampoos, and also preparations that can be administered rectally, such as suppositories, as well as suitable solutions for administration by intravenous infusion, injection, topically or orally, contain from about 0.01 to 99 percent, or from about 0.25 to 75 percent, of a compound of structural formula (I), together with the one or more carriers, excipients, and/or auxiliaries.

The pharmaceutical compositions provided herein can be administered to any patient which may experience the beneficial effects of compounds of structural formula (I). Foremost among such patients are mammals, e.g., humans, although the methods and compositions provided herein are not intended to be so limited. Other patients include veterinary animals (cows, sheep, pigs, horses, dogs, cats and the like).

Compounds of structural formula (I) and pharmaceutical compositions thereof can be administered by any means that achieve their intended purpose. A compound of structural formula (I) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique. Alternatively, or concurrently, administration can be by the oral route. The dosage administered will be dependent upon the age, health, and weight of the recipient, kind of concurrent treatment, if any, frequency of treatment, and the nature of the effect desired.

The present pharmaceutical compositions and preparations are manufactured by conventional mixing, granulating, dragee-making, dissolving, or lyophilizing processes. Pharmaceutical compositions for oral use can be obtained by combining a present compound with solid excipients, optionally grinding the resulting mixture and processing the mixture of granules, after adding suitable auxiliaries, if desired or necessary, to obtain tablets or dragee cores.

Suitable excipients include, for example, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl-starch, cross-linked polyvinyl pyrrolidone, agar, or alginic acid or a salt thereof, such as sodium alginate. Auxiliaries can be suitable flow-regulating agents and lubricants. Suitable auxiliaries include, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions can be used, which optionally can contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds can be dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension including, for example, sodium carboxymethyl cellulose, sorbitol, and/or dextran. Optionally, the suspension may also contain stabilizers.

Topical compositions are formulated in one embodiment as oils, creams, lotions, ointments, and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers can be those in which the active ingredient is soluble. Emulsifiers, stabilizers, humectants and antioxidants also can be included as well as agents imparting color or fragrance, if desired. Additionally, transdermal penetration enhancers can be employed in these topical formulations. Examples of such enhancers can be found in U.S. Pat. Nos. 3,989,816 and 4,444,762, are incorporated herein by reference.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions conveniently are prepared by dissolving the active ingredient, in a suitable high molecular weight alcohol such as propylene glycol or polyethylene glycol.

The following examples are illustrative, but not limiting, of the compounds, compositions, and methods provided herein. Other suitable modifications and adaptations of the variety of conditions and parameters normally encountered in clinical therapy and which are obvious to those skilled in the art are within the spirit and scope of the methods, compounds, and compositions provided herein.

Further provided are kits comprising a compound of structural formula (I) and, optionally, a second therapeutic agent useful in the treatment of diseases and conditions wherein inhibition of MDM2 and MDM2-related proteins provides a benefit, packaged separately or together, and an insert having instructions for using these active agents.

In many embodiments, a compound of structural formula (I) is administered in conjunction with a second therapeutic agent useful in the treatment of a disease or condition wherein inhibition of MDM2 and MDM2-related proteins provides a benefit. The second therapeutic agent is different from the compound of structural formula (I). A compound of structural formula (I) and the second therapeutic agent can be administered simultaneously or sequentially to achieve the desired effect. In addition, the compound of structural formula (I) and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A compound of structural formula (I) and the second therapeutic agent can be administered together as a single-unit dose or separately as multi-unit doses, wherein the compound of structural formula (I) is administered before the second therapeutic agent or vice versa. One or more dose of the compound of structural formula (I) and/or one or more dose of the second therapeutic agent can be administered. The compounds of structural formula (I) therefore can be used in conjunction with one or more second therapeutic agents, for example, but not limited to, anticancer agents.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a compound of structural formula (I) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

As discussed below, MDM2 inhibitors possessed properties that hindered their development as therapeutic agents. In accordance with an important feature of the present invention, compounds of structural formula (I) were synthesized and evaluated as inhibitors of MDM2 and MDM2-related proteins. For example, compounds of the present invention typically have a binding affinity ($IC_{50}$) to MDM2 of less than 50 nM, less than 25 nM, less than 10 nM, and less than 5 nM.

Synthesis of Compounds

Compounds of the present invention were prepared as follows. The following synthetic schemes are representative of the reactions used to synthesize compounds of structural formula (I). Modifications and alternate schemes to prepare MDM2 inhibitors of the invention are readily within the capabilities of persons skilled in the art by substitution of the appropriate reagents and agents in the syntheses shown below.

Solvents and reagents were obtained commercially and used without further purification. Chemical shifts ($\delta$) of NMR spectra are reported as $\delta$ values (ppm) downfield relative to an internal standard, with multiplicities reported in the usual manner.

Unless otherwise stated all temperatures are in degrees Celsius.

In the synthetic methods, the examples, and throughout the specification, the abbreviations have the following meanings

| | |
|---|---|
| min | minutes |
| $CH_2Cl_2$/DCM | methylene chloride |
| MeOH | methanol |
| AcOH | acetic acid |
| MS | mass spectrometry |
| h | hours |
| g | gram |
| HATU | [Bis(dimethylamino)methylene]-1H-1,2,3-triazolo[4,5-b]pyridinium 3-oxid hexafluorophosphate |
| DIEA | N,N-diisopropylethylamine |
| $CH_3CN$ | acetonitrile |
| CDI | carbonyldiimidazole |
| $NaBH(OAc)_3$ | sodium triacetoxyborohydride |
| mol | mole |
| mmol | millimole |
| mL | milliliter |
| $CD_3OD$/MeOD | deuterated methanol |
| M | molar |
| N | normal |
| RT/rt | room temperature |
| NMR | nuclear magnetic resonance spectrometry |
| THF | tetrahydrofuran |
| Hz | Hertz |
| $H_2O$ | water |
| DMAP | 4-dimethylaminopyridine |
| LiOH | lithium hydroxide |
| TLC | thin layer chromatography |
| TFA | trifluoroacetic acid |
| HPLC | high performance liquid chromatography |
| Pd/C | palladium on carbon |

Final compounds are in trifluoroacetate salt form.

Compounds of structural formula (I) can also be prepared by asymmetric synthetic methods, as described in U.S. Pat. Nos. 7,759,383 and 7,737,174 (each incorporated herein by reference), and Ding et al., *J. Am. Chem. Soc.* 127:10130-10131 (2005)). In the case of an asymmetric synthesis, compounds of structural formula (I) can be separated by chiral resolution methods well known in the art, e.g., chiral column chromatography. Suitable chiral columns for use in chiral resolutions include, for example, Daicel CHIRAL-CEL® OD-H, Daicel CHIRAKPAK® AD-H, and Regis Technologies ULMO chiral columns. Other chiral resolution methods are also possible.

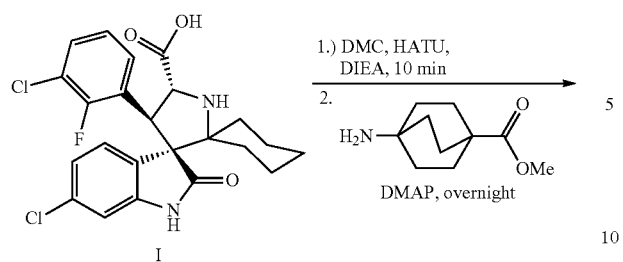

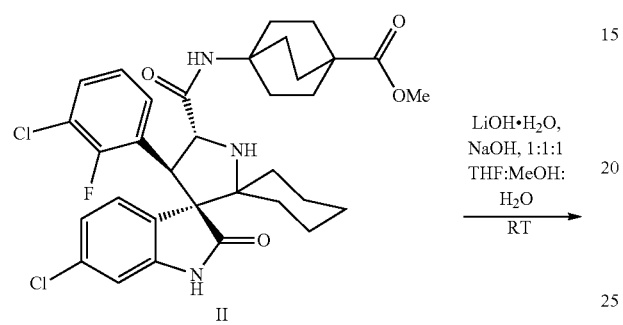

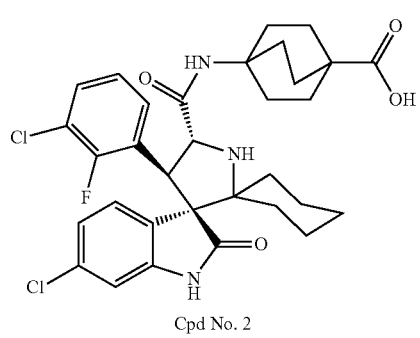

Cpd No. 2

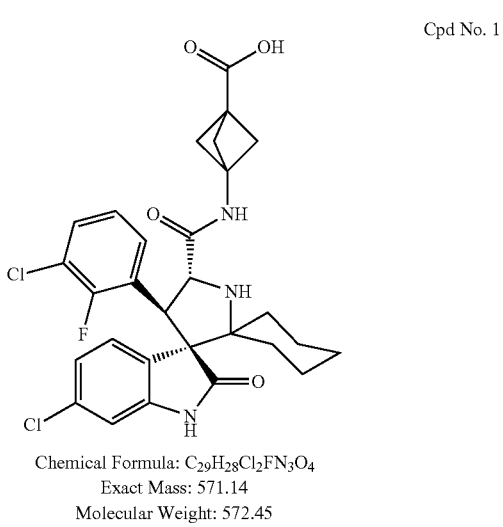 [SMILES: O=C(NC12CC(C(=O)O)(C1)C2)[C@@H]1NC2(CCCCC2)[C@@]2(C(=O)Nc3cc(Cl)ccc32)[C@H]1c1cccc(Cl)c1F]

Cpd No. 1

Chemical Formula: $C_{29}H_{28}Cl_2FN_3O_4$
Exact Mass: 571.14
Molecular Weight: 572.45

Cpd No. 1 was obtained using the same synthetic strategy described for Cpd No. 2. $^1$H-NMR (300 MHz, CD$_3$OD) δ ppm 7.61 (t, J=6.55 Hz, 1H), 7.49 (dd, J=2.34, 8.20 Hz, 1H), 7.39 (t, J=6.90 Hz, 1H), 7.15 (t, J=8.53 Hz, 1H), 7.10 (dd, J=1.94, 8.22 Hz, 1H), 6.78 (d, J=1.88 Hz, 1H), 4.98 (d, J=10.87 Hz, 1H), 4.78 (d, J=10.92 Hz, 1H), 2.84-2.71 (m, 1H), 2.26 (s, 6H), 2.14 (d, J=13.90 Hz, 1H), 2.02-1.67 (m, 5H), 1.60-1.38 (m, 1H), 1.31-1.10 (m, 2H); ESI-MS m/z 572.25 (M+H)$^+$.

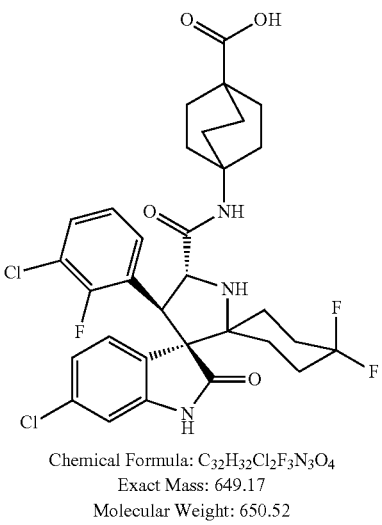

Cpd No. 3

Chemical Formula: $C_{32}H_{32}Cl_2F_3N_3O_4$
Exact Mass: 649.17
Molecular Weight: 650.52

HATU (616 mg, 1.62 mmol), DIEA (0.550 mL, 3.24 mmol) were added to a suspension of acid I (500 mg, 1.08 mmol) in DCM (15 mL) and stirred. After 10 minutes, methyl 4-aminobicyclo[2.2.2]octane-1-carboxylate (396 mg, 2.16 mmol) and DMAP (132 mg, 1.08 mmol) were added to the reaction. After overnight, the solvent was removed in vacuo and the crude was purified by column chromatography to give 549 mg of intermediate II.

LiOH.H$_2$O (110 mg, 2.62 mmol) and sodium hydroxide (105 mg, 2.62 mmol) were added to a solution of intermediate II (549 mg, 0.873 mmol) dissolved in a mixture of THF (3 mL), H$_2$O (3 mL), and MeOH (3 mL). After the hydrolysis was complete, as determined by TLC, the reaction was quenched with TFA (3 mL) and stirred. After 5 minutes, the solution was concentrated in vacuo (not to dryness) and the resulting oil was redissolved in CH$_3$CN and H$_2$O (1:1) and the solution was purified by preparative HPLC. The purified fractions were combined, concentrated in vacuo, re-dissolved in H$_2$O, frozen and lyophilized to give Cpd No. 2 (TFA salt) as a white powder. $^1$H-NMR (300 MHz, CD$_3$OD) δ ppm 7.63 (t, J=6.84 Hz, 1H), 7.45 (d, J=6.76 Hz, 1H), 7.35 (t, J=7.21 Hz, 1H), 7.18-7.04 (m, 2H), 6.77 (dd, J=1.26 Hz, 1H), 4.68 (d, J=10.61 Hz, 1H), 2.73-2.48 (m, 1H), 2.16-1.98 (m, 1H), 1.98-1.43 (m, 18H), 1.27-1.02 (m, 2H); ESI-MS m/z 614.92 (M+H)$^+$.

Cpd No. 3 was obtained using the same synthetic strategy described for Cpd No. 2. $^1$H-NMR (300 MHz, CD$_3$OD) δ ppm 7.71 (s, 1H), 7.63 (t, J=6.61 Hz, 1H), 7.50 (dd, J=2.08, 8.18 Hz, 1H), 7.36 (t, J=7.54 Hz, 1H), 7.18-7.05 (m, 2H), 6.79 (d, J=1.83 Hz, 1H) 4.96 (d, J=10.48 Hz, 1H), 4.71 (d, J=10.51 Hz, 1H), 2.78 (d, J=14.25 Hz, 1H), 2.59-1.91 (m, 6H), 1.91-1.70 (m, 12H), 1.53-1.33 (m, 1H); ESI-MS m/z 650.92 (M+H)$^+$.

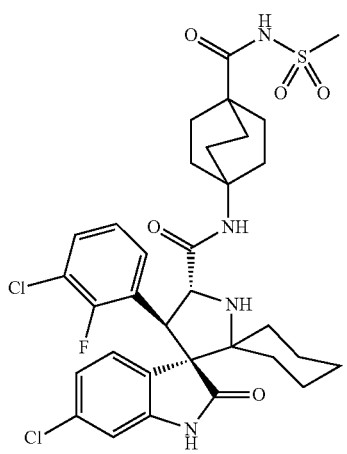

Cpd No. 4

Chemical Formula: $C_{33}H_{37}Cl_2FN_4O_5S$
Exact Mass: 690.18
Molecular Weight: 691.64

Cpd No. 4: CDI (49 mg, 0.303 mmol), DIEA (88 µL, 0.505 mmol), and DMAP (cat.) were added to a solution of Cpd No. 2 (62 mg, 0.101 mmol) in 1,2-dichloroethane (10 mL) and the reaction was heated to 40° C. After 20 minutes, methanesulfonamide (96 mg, 1.01 mmol) was added and the reaction was refluxed. After overnight, the solvent was removed in vacuo and the crude was purified by preparative HPLC to give Cpd No. 4 (TFA salt) as a white solid. $^1$H-NMR (300 MHz, CD$_3$OD) δ ppm 7.64 (t, J=7.23 Hz, 1H), 7.45 (dd, J=1.93, 8.22 Hz, 1H), 7.36 (t, J=7.23 Hz, 1H), 7.18-7.04 (m, 2H), 6.77 (d, J=1.66 Hz, 1H), 4.69 (d, J=10.70 Hz, 1H), 3.19 (s, 3H), 2.75-2.52 (m, 1H), 2.21-1.99 (m, 1H), 1.99-1.44 (m, 17H), 1.41-1.27 (m, 1H), 1.27-1.03 (m, 2H); ESI-MS m/z 691.42 (M+H)$^+$.

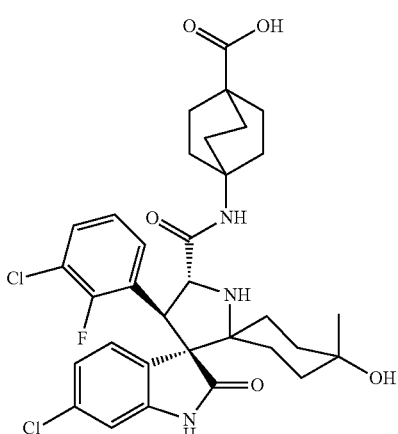

Cpd No. 5

Chemical Formula: $C_{33}H_{36}Cl_2FN_3O_5$
Exact Mass: 643.20
Molecular Weight: 644.56

Cpd No. 5 was obtained using the same synthetic strategy described for Cpd No. 2. $^1$H-NMR (300 MHz, CD$_3$OD) δ ppm 7.69-7.60 (m, 2H), 7.48 (, dd, J=2.09, 8.23 Hz, 1H), 7.40 (t, J=6.93 Hz, 1H), 7.16 (t, J=8.05 Hz, 1H), 7.09 (dd, J=1.91, 8.21 Hz, 1H), 6.79 (d, J=1.87 Hz, 1H), 5.07 (d, J=11.01 Hz, 1H), 4.72 (d, J=11.08 Hz, 1H), 2.60 (d, J=12.07 Hz, 1H), 2.30 (dt, J=4.11, 13.45 Hz, 1H), 2.11-1.93 (m, 2H), 1.92-1.52 (m, 16H), 1.25 (s, 3H); ESI-MS m/z 644.25 (M+H)$^+$.

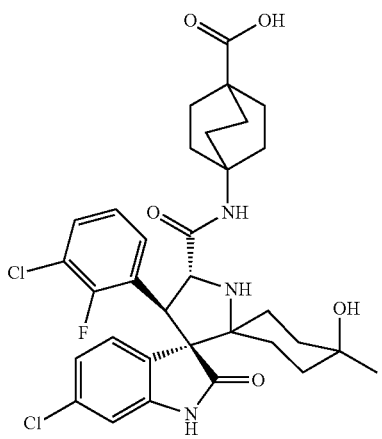

Cpd No. 6

Chemical Formula: $C_{33}H_{36}Cl_2FN_3O_5$
Exact Mass: 643.20
Molecular Weight: 644.56

Cpd No. 6 was obtained using the same synthetic strategy described for Cpd No. 2. $^1$H-NMR (300 MHz, CD$_3$OD) δ ppm 7.70 (s, 1H), 7.62 (t, J=7.05 Hz, 1H), 7.52 (dd, J=2.08, 8.21 Hz, 1H), 7.38 (t, J=7.41 Hz, 1H), 7.15 (d, J=7.93 Hz, 1H), 7.10 (dd, J=1.76, 8.19 Hz, 1H), 6.79 (d, J=1.83 Hz, 1H), 4.99 (d, J=11.35 Hz, 1H), 4.70 (d, J=11.00 Hz, 1H), 2.76-2.59 (m, 1H), 2.22-1.91 (m, 3H), 1.89-1.19 (m, 16H), 1.03 (s, 3H); ESI-MS m/z 644.75 (M+H)$^+$.

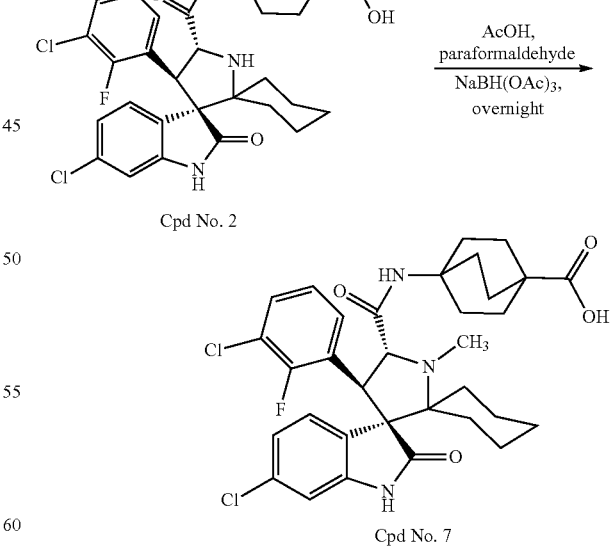

Cpd No. 2

AcOH, paraformaldehyde
NaBH(OAc)$_3$,
overnight

Cpd No. 7

Paraformaldehyde (15 mg, 0.506 mmol) was added to a solution of compound Cpd No. 2 (20 mg, 0.028 mmol) dissolved in AcOH (1 mL). After 15 minutes sodium triacetoxyborohydride (59 mg, 0.28 mmol) was added and after reacting overnight the reaction was quenched with saturated ammonium chloride solution and extracted with ethyl acetate. The ethyl acetate solvent was removed in vacuo and the resulting oil was re-dissolved in a solution of acetonitrile and water (1:1 with 0.1% TFA) and purified by preparative HPLC. The pure Cpd No. 7 fractions were combined, concentrate in vacuo, re-dissolved in water (with minimum amount of acetonitrile), frozen and lyophilized to give Cpd No. 7 (TFA salt) as a white powder. $^1$H-NMR (300 MHz, CD$_3$OD) δ ppm 7.94 (s, 1H), 7.61-7.52 (m, 2H), 7.40 (t, J=7.32 Hz, 1H), 7.19-7.08 (m, 2H), 6.78 (d, J=1.56 Hz, 1H), 4.99 (d, J=11.86 Hz, 1H), 4.63 (d, J=12.06 Hz, 1H), 3.27 (s, 3H), 2.61-2.48 (m, 1H), 2.32-2.14 (m, 2H), 1.88-1.40 (m, 18H), 1.37-1.12 (m, 1H); ESI-MS m/z 628.83 (M+H)$^+$.

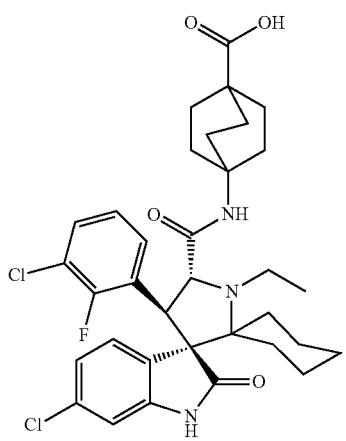

Cpd No. 8

Chemical Formula: C$_{34}$H$_{38}$Cl$_2$FN$_3$O$_4$
Exact Mass: 641.22
Molecular Weight: 642.59

Cpd No. 8 was obtained using the same synthetic strategy described for Cpd No. 7. $^1$H-NMR (300 MHz, CD$_3$OD) δ ppm 7.63 (t, J=7.04 Hz, 1H), 7.56-7.48 (m, 2H), 7.42 (t, J=7.39 Hz, 1H), 7.18 (t, J=7.96 Hz, 1H), 7.10 (d, J=8.06 Hz, 1H), 6.79 (s, 1H), 5.08-4.96 (m, 1H), 4.57 (d, J=11.85 Hz, 1H), 4.18-3.99 (m, 1H), 3.87-3.69 (m, 1H), 2.70-2.54 (m, 1H), 2.36-2.13 (m, 2H), 1.94-1.45 (m, 18H), 1.39 (t, J=6.65 Hz, 3H), 1.32-1.14 (m, 1H); ESI-MS m/z 642.50 (M+H)$^+$.

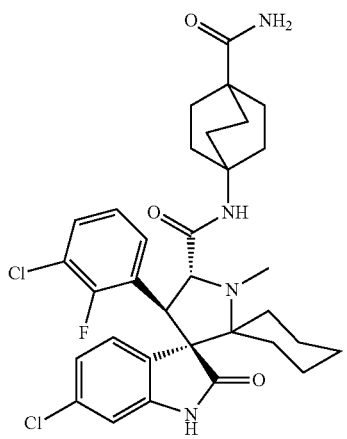

Cpd No. 9

Chemical Formula: C$_{33}$H$_{37}$Cl$_2$FN$_4$O$_3$
Exact Mass: 626.22
Molecular Weight: 627.58

Cpd No. 9 was obtained using the same synthetic strategy described for Cpd No. 4 (ammonium hydroxide solution was added instead of methanesulfonamide). $^1$H-NMR (300 MHz, CD$_3$OD) δ ppm; ESI-MS m/z 627.58 (M+H)$^+$.

To demonstrate the ability of the present MDM2 inhibitors to bind to MDM2 proteins, competitive FP binding assays were performed. Stability tests, cell growth assays, pharmacokinetic studies, and in vivo efficacy studies in SJSA-1 xenograft models using the present MDM2 inhibitors also were performed.

Fluorescence-Polarization MDM2 Binding Assay

The binding affinity of the MDM2 inhibitors disclosed herein was determined using a fluorescence polarization-based (FP-based) binding assay using a recombinant human His-tagged MDM2 protein (residues 1-118) and a fluorescently tagged p53-based peptide.

The design of the fluorescence probe was based upon a previously reported high-affinity p53-based peptidomimetic compound called PMDM6-F (García-Echeverría et al., *J. Med. Chem.* 43: 3205-3208 (2000)). The K$_d$ value of PMDM6-F with the recombinant MDM2 protein was determined from the saturation curve. MDM2 protein was serially double diluted in a Dynex 96-well, black, round-bottom plate, and the PMDM6-F peptide was added at 1 nM concentration. The assay was performed in the buffer: 100 mM potassium phosphate, pH 7.5; 100 μg/mL bovine gamma globulin; 0.02% sodium azide, 0.01% Triton X-100) and the polarization values were measured after 3 h of incubation using an ULTRA READER (Tecan U.S. Inc., Research Triangle Park, NC). The IC$_{50}$ value was obtained by fitting the mP values in a sigmoidal dose-response curve (variable slope) with a non-linear regression, and was determined to be 1.40 nM±0.25. The K$_d$ value was calculated using the equation: K$_d$ value=IC$_{50}$−L0/2. L0/2 is the concentration of the free ligand (PMDM6-F). Since PMDM6-F was used at a final concentration of 1 nM, L0/2 was 0.5 nM.

Dose-dependent, competitive binding experiments were performed with serial dilutions of a tested compound in DMSO. A 5 μL sample of the tested compound and pre-incubated MDM2 protein (10 nM) and PMDM6-F peptide (1 nM) in the assay buffer (100 mM potassium phosphate, pH 7.5; 100 μg/mL bovine gamma globulin; 0.02% sodium azide, 0.01% Triton X-100), were added in a Dynex 96-well, black, round-bottom plate to produce a final volume of 125 μL. For each assay, the controls included the MDM2 protein and PMDM6-F (equivalent to 0% inhibition), PMDM6-F peptide alone (equivalent to 100% inhibition). The polarization values were measured after 3 h of incubation. The IC$_{50}$ values, i.e., the inhibitor concentration at which 50% of bound peptide is displaced, were determined from a plot using nonlinear least-squares analysis. Curve fitting was performed using GRAPHPAD PRISM software (GraphPad Software, Inc., San Diego, Calif.). The results of this assay are summarized in Table 2.

Cell Growth Assay

Isogenic HCT-116 colon cancer cell lines were a kind gift from Prof. Bert Vogelstein (Johns Hopkins, Baltimore, Md.) and were maintained in McCoy's 5A medium containing 10% FBS. The SJSA-1 cell lines were obtained from ATCC, (Manassas, Va.) and were maintained in RPMI-1640 medium containing 10% FBS.

Cells were seeded in 96-well flat bottom cell culture plates at a density of 2-3×10$^3$ cells/well with compounds and incubated for 4 days. The rate of cell growth inhibition after treatment with increasing concentrations of the tested compounds was determined by WST-8 (2-(2-methoxy-4-nitrophenyl)-3-(4-nitrophenyl)-5-(2,4-disulfophenyl)-2H-tetrazolium monosodium salt (Dojindo Molecular Technologies Inc., Gaithersburg, Md.). WST-8 was added at a final concentration of 10% to each well, and then the plates were incubated at 37° C. for 2-3 hrs. The absorbance of the samples was measured at 450 nm using a TECAN ULTRA Reader. The concentration of the compounds that inhibited cell growth by 50% (IC$_{50}$) was calculated by comparing absorbance in the untreated cells and the cells treated with the compounds using the GraphPad Prism software (GraphPad Software, La Jolla, Calif. 92037, USA). The results of this assay are presented in Table 2.

TABLE 2

| Compound ID | Chemical Structure | MDM2 (FP binding assay) | | Cell Growth Inhibition IC50 (μM) | | |
|---|---|---|---|---|---|---|
| | | IC$_{50}$(nM) | K$_i$(nM) | SJSA-1 | HCT116 p53 WT | HCT116 p53 deleted |
| (1) | [structure] | 5.4 | <1 | 0.48 | 3.7 | 12.6 |
| (2) | [structure] | 5.2 | <1 | 0.089 ± 0.033 | 0.137 ± 0.031 | 14.0 ± 2 |
| (3) | [structure] | 8.8 | <1 | 0.165 | | |

TABLE 2-continued

| Compound ID | Chemical Structure | MDM2 (FP binding assay) | | Cell Growth Inhibition IC50 (μM) | | |
|---|---|---|---|---|---|---|
| | | IC$_{50}$(nM) | K$_i$(nM) | SJSA-1 | HCT116 p53 WT | HCT116 p53 deleted |
| (4) | [structure] | 7.9 | <1 | 0.373 | | |
| (5) | [structure] | 131 | 30 | | | |
| (6) | [structure] | 7.3 | <1 | | | |

TABLE 2-continued

| Compound ID | Chemical Structure | MDM2 (FP binding assay) | | Cell Growth Inhibition IC50 (μM) | | |
|---|---|---|---|---|---|---|
| | | IC$_{50}$(nM) | K$_i$(nM) | SJSA-1 | HCT116 p53 WT | HCT116 p53 deleted |
| (7) | | 4.5 | <1 | 0.070 ± 0.021 | 0.117 ± 0.033 | 18.0 ± 8 |
| (8) | | 3.8 | <1.0 | 0.060 ± 0.022 | 0.104 ± 0.036 | 8.0 ± 1 |
| (9) | | 5.2 | <1.0 | 0.173 ± 0.031 | 0.266 ± 0.127 | 9.0 ± 1 |

In Vivo Efficacy Studies Using SJSA-Xenograft Models

SJSA-1 (osteosarcoma) tumor cells were harvested with Trypsin (0.05%)-EDTA (0.53 mM) (GIBCO™, Invitrogen Corp.), growth medium was added, and the cells were placed on ice. A cell sample was mixed 1:1 with Trypan Blue (GIBCO™, Invitrogen Corp.) and counted on a hemocytometer to determine the number of live/dead cells. Cells were washed once with 1×PBS (GIBCO™, Invitrogen Corp.) and resuspended in PBS. For Matrigel injections, after washing in PBS, cells are resuspended in an ice cold mixture of 1:1 PBS and Matrigel (BD Biosciences, Invitrogen Corp.) for a final Matrigel protein concentration of 5 mg/ml. SJSA-1 tumors were inoculated into C.B-17 SCID mice at 5×10$^6$ cells in 0.1 ml with Matrigel. Cells were injected s.c. into the flank region of each mouse using a 27 gauge needle.

The size of tumors growing in the mice was measured in two dimensions using calipers. Tumor volume (mm$^3$)=(A× B$^2$)/2 where A and B are the tumor length and width (in mm), respectively. During treatment, tumor volume and body weight was measured three times a week. After the treatment was stopped, tumor volume and body weight was measured at least once a week. Mice were kept for an additional 60 days for further observation of tumor growth and toxicity. The anti-tumor activity of compounds No. 1, No. 7 and No. 8 are shown in FIG. 2. The anti-tumor activity of compound No. 8 (administered via oral gavage) at different doses and according to different dosing schedules, including weekly for 3 weeks (qw*3 wks), every other day for 3 weeks, daily for 3 days out of a week for 3 weeks (qd1-3/w*3 wks), and daily for 2 weeks (qd*14 d), is shown in FIG. 3.

Suitable vehicles for in vivo administration of the compounds provided herein include, without limitation, 10% PEG 400:3% Cremophor:87% PBS; 98% PEG 200:2% polysorbate 80; 98% PEG 200:2% TPGS; and 0.5% polysorbate 80:0.6% methyl cellulose:98.9% water.

Stability of Compounds in Solution

The stability of the compounds were determined in 1:1 MeOH:H$_2$O, 1:1 CH$_3$CN:H$_2$O, and cell culture medium using ultra performance liquid chromatography.

The following Tables 3, 4, and 5 summarize additional test results showing the microsomal stability, oral pharmakinetics, and cell growth inhibition for compounds Cpd No. 2, Cpd No. 7, and Cpd No. 8.

TABLE 3

Microsomal stability of representative compounds in mouse, rat, dog and human microsomes

| | T$_{1/2}$ (min) | | | |
|---|---|---|---|---|
| Compound | Mouse | Rat | Dog | Human |
| Cpd No. 2 | >60 | >60 | >60 | >60 |
| Cpd No. 7 | >60 | >60 | >60 | >60 |
| Cpd No. 8 | >60 | >60 | >60 | >60 |

TABLE 4

Summary of oral Pharmacokinetic data in Sprague-Dawley Rats

| Compound | Dose (mg/kg) | route | Cmax(ng/mL) | Tmax (h) | AUC0-t (ng · h/mL) | AUC0-∞(ng · h/mL) | t$_{1/2}$ (h) | F(AUC0-∞) |
|---|---|---|---|---|---|---|---|---|
| Cpd No. 2 | 25 | oral | 8234 ± 278 | 3.33 ± 1.15 | 73603 ± 5022 | 74319 ± 5260 | 4.29 ± 0.371 | 35.0 ± 2.48 |
| Cpd No. 7 | 25 | oral | 4391 ± 2826 | 4.00 ± 0.0 | 35205 ± 15223 | 35426 ± 15489 | 3.89 ± 1.02 | 48.6 ± 21.3 |
| Cpd No. 8 | 25 | oral | 5453 ± 894 | 4.00 ± 0.0 | 39083 ± 8473 | 39528 ± 8521 | 4.61 ± 1.35 | 40.3 ± 8.69 |

TABLE 5

Inhibition of cell growth by representative compounds. Cells were treated for 4 days and cell growth was determined using WST assay.

| | | | Compound ID | | |
|---|---|---|---|---|---|
| | | | Compound No. 2 | Compound No. 7 | Compound No. 8 |
| Cell Lines | Tumor Type | p53 Status | Cell Growth Inhibition (IC50) | | |
| SJSA-1 | Osteosarcoma | Wild-type | 89 ± 33 (nM) | 70 ± 21 (nM) | 60 ± 22 (nM) |
| Saos2 | Osteosarcoma | Null | 26.7 ± 5.1 (μM) | 25 ± 6 (μM) | 22.7 ± 4.7 (μM) |
| RS4; 11 | Leukemia | Wild-type | 62 ± 26 (nM) | 56 ± 18 (nM) | 38 ± 5 (nM) |
| LNCaP | Prostate Cancer | Wild-type | 36 ± 19 (nM) | 30 ± 15 (nM) | 18 ± 13 (nM) |
| PC3 | Prostate Cancer | Null | 12.3 ± 2.5 (μM) | 24 ± 5 (μM) | 22 ± 7.2 (μM) |
| HCT116 | Colon Cancer | Wild-type | 137 ± 31 (nM) | 117 ± 33 (nM | 104 ± 36 (nM) |
| HCT116 p53−/− | Colon Cancer | Knock-out | 14 ± 2 (μM) | 18 ± 8 (μM) | 8 ± 1 (μM) |
| ZR-75-1 | Breast Cancer | Wild-type | 677 ± 252 (nM) | 713 ± 165 (nM) | 462 ± 36 (nM) |

The present invention encompasses compounds of structural formula (I) and pharmaceutical compositions comprising a compound of structural formula (I) and a pharmaceutically acceptable carrier.

The present invention also encompasses a method of treating a patient comprising administering to the patient a therapeutically effective amount of the compound of structural formula (I), wherein the patient has a hyperproliferative disease, wherein cells of the hyperproliferative disease, such as a cancer, express functional p53, further comprise administering to the patient one or more anticancer agents e.g., a chemotherapeutic agent or radiation therapy.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed:

1. A compound having the structural formula:

wherein:

is selected from the group consisting of

B is a $C_{4-7}$ carbocyclic ring;
$R_1$ is H, substituted or unsubstituted $C_{1-4}$alkyl, substituted or unsubstituted cycloalkyl, substituted or unsubstituted heterocycloalkyl, $OR^a$, or $NR^aR^b$;
n is 0, 1, or 2;
$R_2$, $R_3$, $R_4$, $R_5$, $R_7$, $R_8$, $R_9$, and $R_{10}$, independently, are selected from the group consisting of H, F, Cl, $CH_3$, and $CF_3$;
$R_6$ is $R^a$ is hydrogen or substituted or unsubstituted $C_{1-4}$alkyl;
$R^b$ is hydrogen or substituted or unsubstituted $C_{1-4}$alkyl;
$R^c$ and $R^d$ are substituents on one carbon atom of ring B, wherein
$R^c$ is H, $C_{1-3}$alkyl, $C_{1-3}$alkyleneOR$^a$, $OR^a$, or halo;
$R^d$ is H, $C_{1-3}$alkyl, $C_{1-3}$alkyleneOR$^a$, $OR^a$, or halo;
and
$R^e$ is —C(=O)OR$^a$, —C(=O)NR$^a$R$^b$, or —C(=O)NHSO$_2$CH$_3$, or
a pharmaceutically acceptable salt thereof.

2. The compound of claim 1, wherein is

3. The compound of claim 1, wherein B is

4. The compound of claim 1, wherein n is 0 or 1.
5. The compound of claim 4, wherein $R_1$ is H or $CH_3$.
6. The compound of claim 1, wherein —$(CH_2)_n$—$R_1$ is H, $CH_3$, or $CH_2CH_3$.
7. The compound of claim 1, wherein $R_2$ is H.
8. The compound of claim 1, wherein $R_3$ is halo.
9. The compound of claim 8, wherein $R_3$ is chloro.
10. The compound of claim 1, wherein $R_4$ is H.
11. The compound of claim 1, wherein $R_5$ is H.

12. The compound of claim 1, wherein $R_4$ and $R_5$ are H.

13. The compound of claim 1, wherein $R_7$ is halo.

14. The compound of claim 13, wherein $R_7$ is fluoro.

15. The compound of claim 1, wherein each of $R_8$, $R_9$, and $R_{10}$ is H.

16. The compound of claim 1, wherein $R^a$ and $R^b$, individually, are H, $CH_3$, or $CH_2CH_3$.

17. The compound of claim 1, wherein $R^c$ and $R^d$, individually, are H, halo, OH, $CH_3$, $CH_2CH_3$, or $CH_2OH$.

18. The compound of claim 1, wherein $R^c$ and $R^d$ are F and F, H and H, OH and $CH_3$, OH and H, $CH_3$ and $CH_3$, $CH_3$ and OH, H and OH, $CH_2CH_3$ and $CH_2CH_3$, or $CH_2OH$ and $CH_2OH$.

19. The compound of claim 1, wherein $R^c$ and $R^d$ taken together with ring B form:

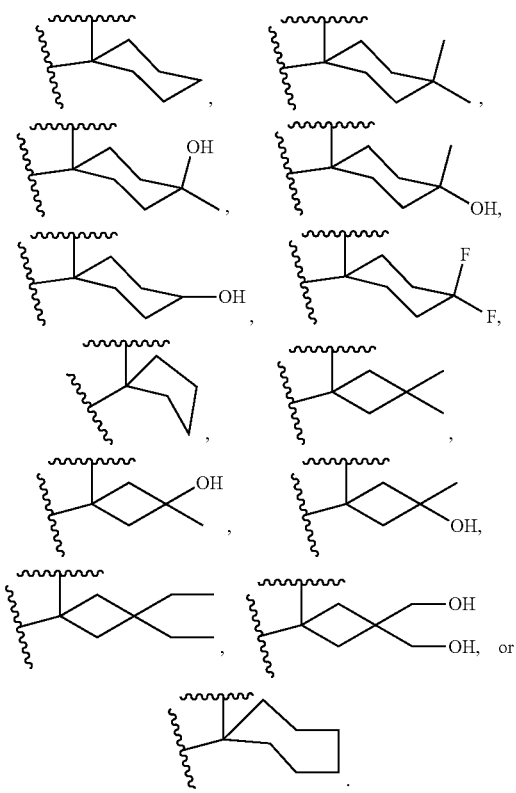

20. The compound of claim 1, wherein $R^e$ is —C(=O)OH, —C(=O)NH$_2$, or —C(=O)NHSO$_2$CH$_3$.

21. The compound of claim 1, wherein $R^6$ is

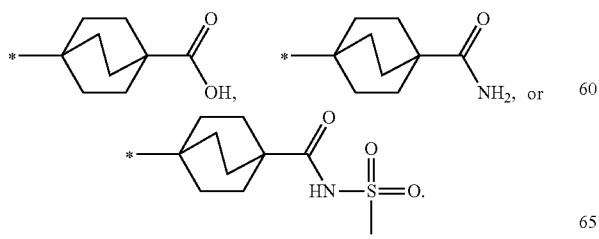

22. A compound selected from the group consisting of

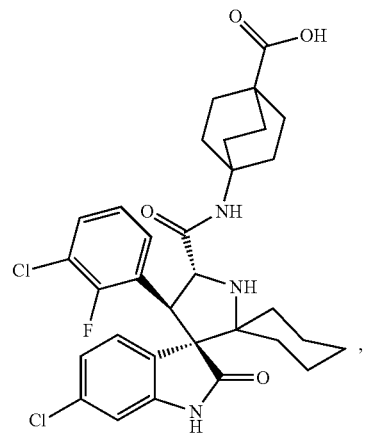

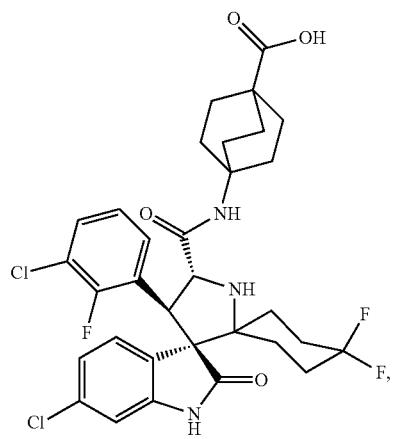

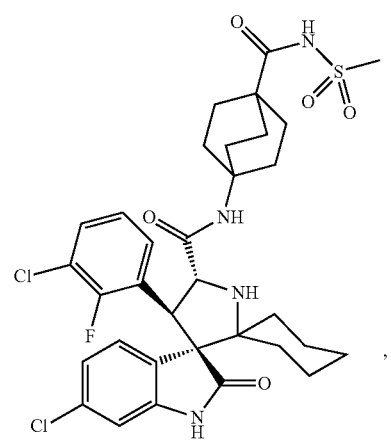

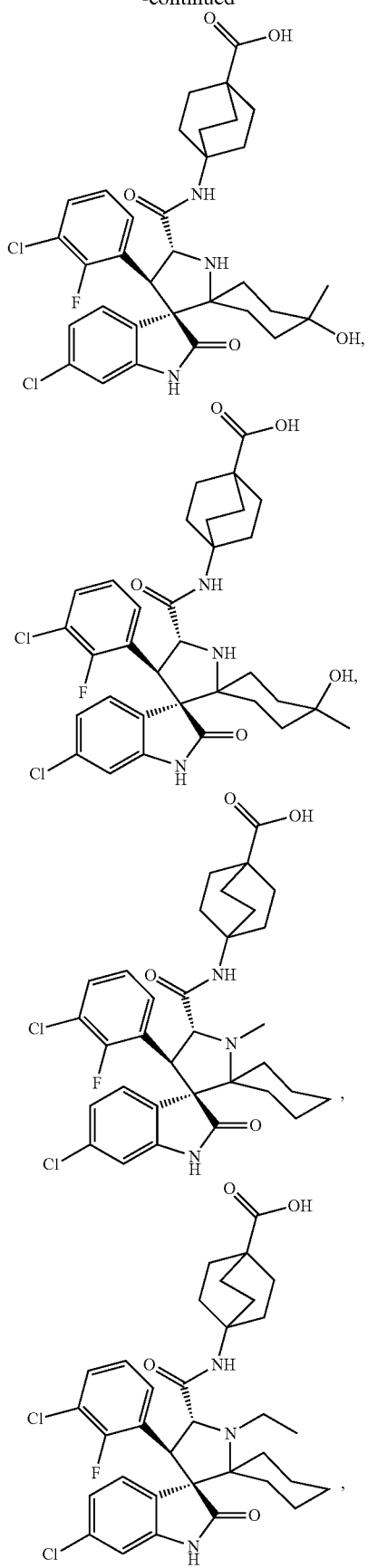
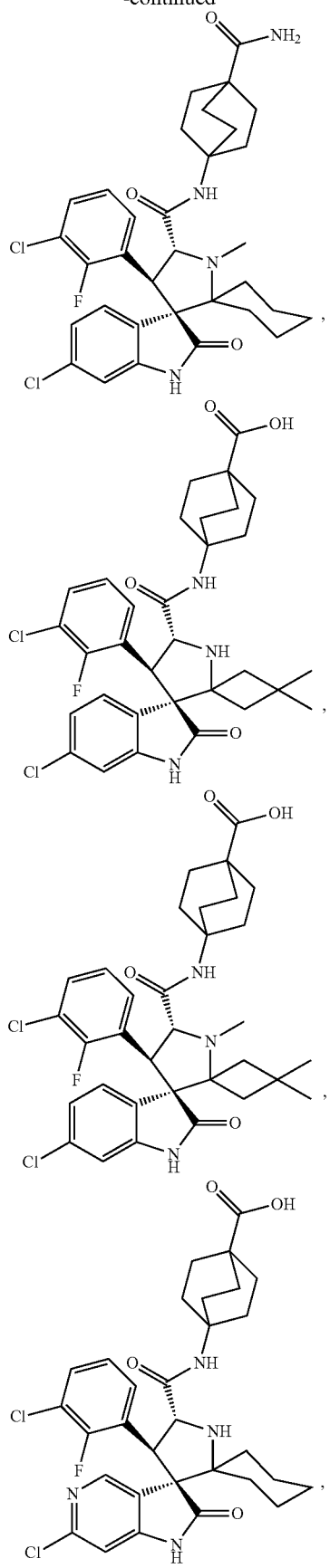

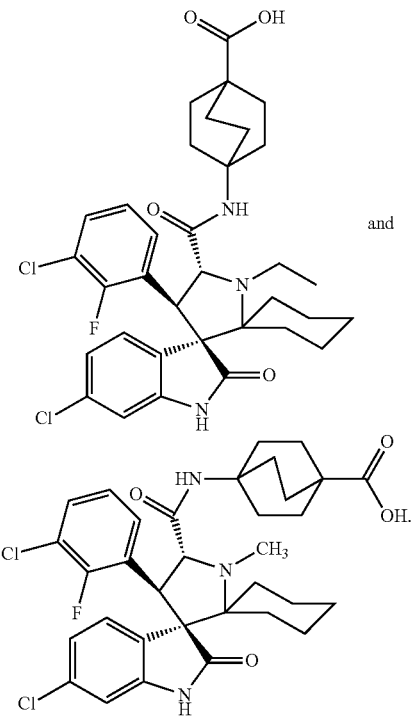

23. A composition comprising (a) a compound of claim 1 and (b) an excipient and/or a pharmaceutically acceptable carrier.

24. The composition of claim 23, further comprising a chemotherapeutic agent useful in the treatment of a hyperproliferative disease.

25. The compound of claim 1, wherein

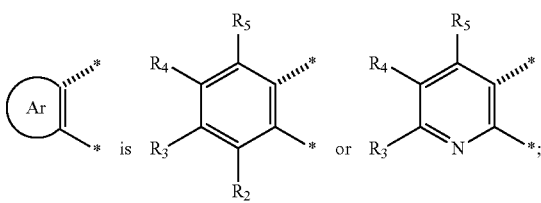

B is

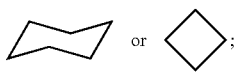

—(CH$_2$)$_n$—R$_1$ is H, CH$_3$, or CH$_2$CH$_3$;
R$_2$, R$_3$, R$_4$, R$_5$, R$_8$, R$_9$, and R$_{10}$, independently, are selected from the group consisting of H, F, Cl, and CH$_3$;
R$_7$ is F; and
R$_6$ is

26. A compound selected from the group consisting of

* * * * *

UNITED STATES PATENT AND TRADEMARK OFFICE
CERTIFICATE OF CORRECTION

PATENT NO. : 9,745,314 B2  
APPLICATION NO. : 14/688553  
DATED : August 29, 2017  
INVENTOR(S) : Shaomeng Wang et al.

Page 1 of 1

It is certified that error appears in the above-identified patent and that said Letters Patent is hereby corrected as shown below:

Column 1, Line 10:
Please insert:
--STATEMENT OF GOVERNMENT SUPPORT
This invention was made with government support under CA121279 awarded by the National Institutes of Health. The government has certain rights in the invention.--

Signed and Sealed this
Tenth Day of October, 2017

Joseph Matal
*Performing the Functions and Duties of the*
*Under Secretary of Commerce for Intellectual Property and*
*Director of the United States Patent and Trademark Office*